United States Patent
Nishioka et al.

(10) Patent No.: US 10,874,306 B2
(45) Date of Patent: Dec. 29, 2020

(54) SOFT GRIPPER AND BLOOD PRESSURE MEASURING CUFF COMPRISING THE SAME

(71) Applicants: OMRON HEALTHCARE CO., LTD., Muko (JP); THE UNIVERSITY OF SHIGA PREFECTURE, Hikone (JP); OMRON CORPORATION, Kyoto (JP)

(72) Inventors: Yasutaka Nishioka, Shiga (JP); Wataru Masuda, Shiga (JP); Masao Shimizu, Kyoto (JP); Tsuyoshi Hamaguchi, Kyoto (JP); Minoru Taniguchi, Kyoto (JP)

(73) Assignees: OMRON HEALTHCARE CO., LTD., Muko (JP); UNIVERSITY OF SHIGA PREFECTURE, Hikone (JP); OMRON CORPORATION, Kyoto (JP)

(*) Notice: Subject to any disclaimer, the term of this patent is extended or adjusted under 35 U.S.C. 154(b) by 255 days.

(21) Appl. No.: 15/989,627

(22) Filed: May 25, 2018

(65) Prior Publication Data
US 2018/0271386 A1 Sep. 27, 2018

Related U.S. Application Data

(63) Continuation of application No. PCT/JP2016/066941, filed on Jun. 7, 2016.

(30) Foreign Application Priority Data

Nov. 30, 2015 (JP) .................................. 2015-234101

(51) Int. Cl.
A61B 5/021 (2006.01)
A61B 5/022 (2006.01)

(52) U.S. Cl.
CPC .......... *A61B 5/02141* (2013.01); *A61B 5/022* (2013.01); *A61B 5/02116* (2013.01); *A61B 5/02233* (2013.01)

(58) Field of Classification Search
CPC ....................... A61B 5/021–0235; B25J 9/142
See application file for complete search history.

(56) References Cited

U.S. PATENT DOCUMENTS

| | | | | |
|---|---|---|---|---|
| 2014/0109560 A1* | 4/2014 | Ilievski | .................... | B25J 9/142 60/327 |
| 2015/0090113 A1* | 4/2015 | Galloway | ............. | F15B 15/103 92/48 |

(Continued)

FOREIGN PATENT DOCUMENTS

| CN | 104125800 A | 10/2014 |
|---|---|---|
| JP | 2006-198280 A | 8/2006 |

(Continued)

OTHER PUBLICATIONS

Aug. 16, 2016 International Search Report issued in International Patent Application No. PCT/JP2016/066941.

(Continued)

*Primary Examiner* — Thaddeus B Cox
(74) *Attorney, Agent, or Firm* — Oliff PLC

(57) ABSTRACT

A soft gripper that surrounds and grips an outer peripheral surface of an object, the soft gripper includes an elongated first actuator and an elongated second actuator, which are deformed in response to supply of a fluid. The first actuator and the second actuator extend from bases of the first and second actuators toward opposite sides each other. When receiving the supply of the fluid, each of the first and second actuators sequentially surrounds the object from the base toward a side of a leading end of the each of the first and second actuators.

13 Claims, 30 Drawing Sheets

(56) References Cited

U.S. PATENT DOCUMENTS

| | | | |
|---|---|---|---|
| 2015/0091711 A1* | 4/2015 | Kosonen | G08B 6/00 340/407.1 |
| 2015/0257839 A1* | 9/2015 | Vause | B25J 15/12 606/130 |
| 2015/0257968 A1* | 9/2015 | Vause | A61H 9/0007 601/11 |
| 2016/0075036 A1* | 3/2016 | Lessing | B25J 15/10 361/234 |

FOREIGN PATENT DOCUMENTS

| | | | |
|---|---|---|---|
| JP | 2010-110846 A | 5/2010 | |
| JP | 2013-220321 A | 10/2013 | |
| WO | 91/08705 A1 | 6/1991 | |
| WO | 2015/050852 A1 | 4/2015 | |

OTHER PUBLICATIONS

Ilievski, et al. "Soft Robotics for Chemists". Chemical Robotics, Angewandte Chemie International Edition, vol. 50 No. 8, pp. 890-1895, 2011.

Shepherd, et al. "Multigait Soft Robot". Proceedings of the National Academy of Sciences of the United States of America, vol. 105, No. 51, 2011, pp. 20400-20403 and 1-7.

May 23, 2019 extended European Search Report issued in Eupoean Patent Application No. 16870217.3.

May 31, 2018 International Preliminary Report on Patentability issued in International Patent Application No. PCT/JP2016/066941.

Jun. 10, 2020 Office Action issued Chinese Patent Application No. 201680069380.1.

* cited by examiner t = t1 t = t11 t = t12 t = t13

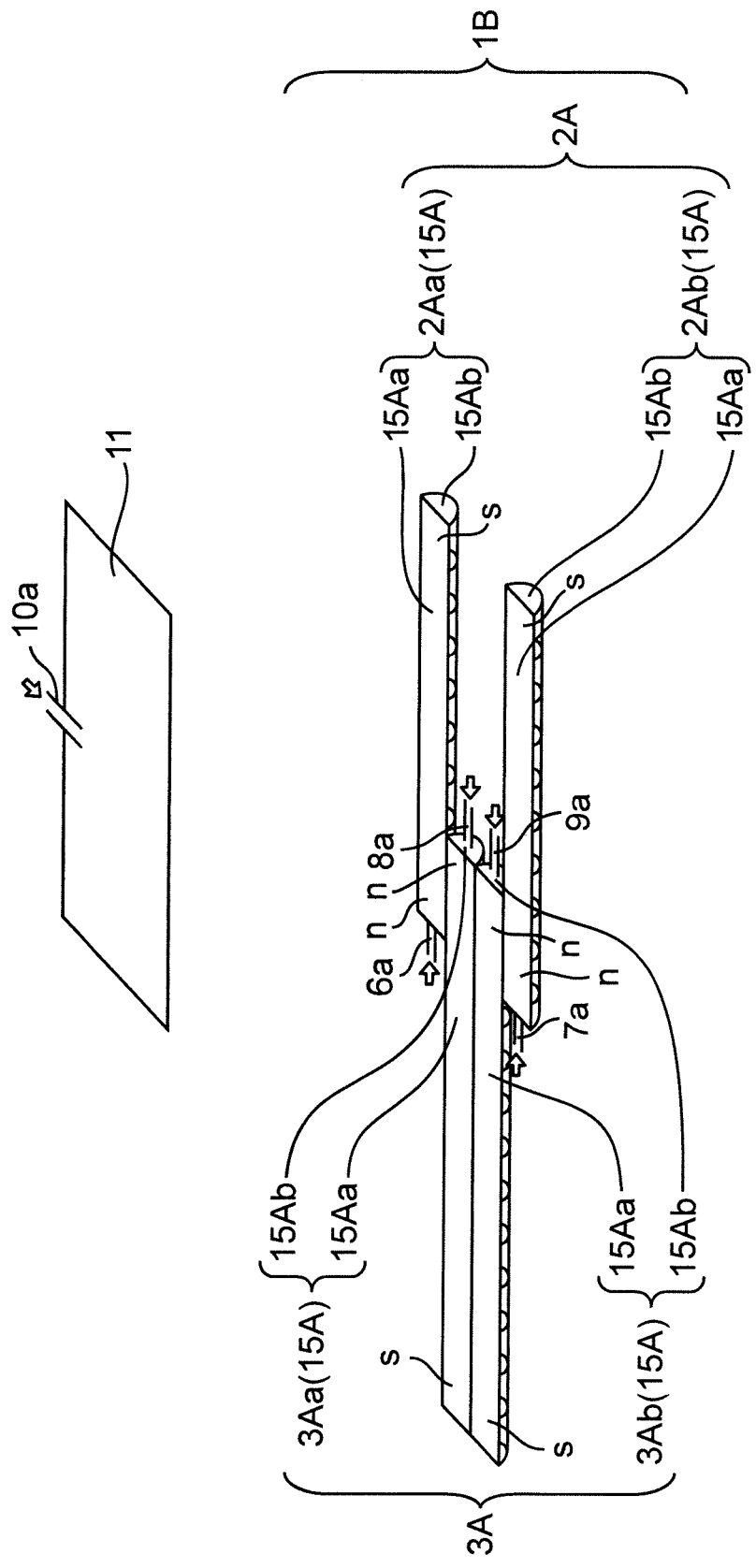

SOFT GRIPPER AND BLOOD PRESSURE MEASURING CUFF COMPRISING THE SAME

CROSS-REFERENCE TO RELATED APPLICATIONS

This is a continuation application of International Application No. PCT/JP2016/066941, with an International filing date of Jun. 7, 2016, which claims priority of Japanese Patent Application No. 2015-234101 filed on Nov. 30, 2015, the entire content of which is hereby incorporated by reference.

TECHNICAL FIELD

The present invention relates to a soft gripper, more particularly to a soft gripper that automatically surrounds and grips an object using air pressure. The present invention also relates to a blood pressure measuring cuff provided with the soft gripper.

BACKGROUND ART

In recent years, Japan is approaching a super-aging society. High-blood pressure diseases are cited as injuries and/or diseases with a high rate of treatment accepter for the elderly. Health care by the elderly themselves is regarded as important, and many people use commercially available mobile type sphygmomanometers at home in recent years. For example, Patent Literature 1 (JP 2013-220321 A) discloses that a subject wears a blood pressure measuring cuff while wrapping the blood pressure measuring cuff around an upper arm during measurement.

SUMMARY OF INVENTION

However, it is difficult for the elderly and those having diseases of the shoulder to tighten or detach the blood pressure measuring cuff by themselves. Typically, the elderly and women have a small arm diameter, while in Western countries, sometimes people have an arm diameter large enough not to fix the conventional blood pressure measuring cuff. The thickness of the arm varies by people, and therefore, it was difficult to address these problems.

An object of the present invention is to provide a soft gripper that can automatically surround and grip the object while adapting to the thickness of the object (including a region to be measured such as the arm). Another object of the present invention is to provide a blood pressure measuring cuff, which includes the soft gripper and can be mounted by automatically surrounding the region to be measured.

In order to solve the above problem, the soft gripper for fixing a human body of the present disclosure comprises:

an elongated first actuator and an elongated second actuator, which are deformed in response to supply of a fluid;

wherein the first actuator and the second actuator extend from bases of the first and second actuators toward opposite sides to each other, and when receiving the supply of the fluid in a condition that the base or a specific point between the base and a leading end is contact with the object, each of the first and second actuators is deformed along with the outer peripheral surface of the object to surround the object by starting to be bent sequentially from the base or the specific point toward a side of the leading end.

As used herein, the "base" means an end on the side of a connection portion where the first actuator and the second actuator are connected to each other. The "leading end" means an end on the opposite side to the "base".

In another aspect, a blood pressure measuring cuff of the present disclosure comprises the above described soft gripper.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 15 is an exploded perspective view illustrating the structure of the blood pressure measuring cuff in FIG. 14.

DESCRIPTION OF EMBODIMENTS

Figure 1:
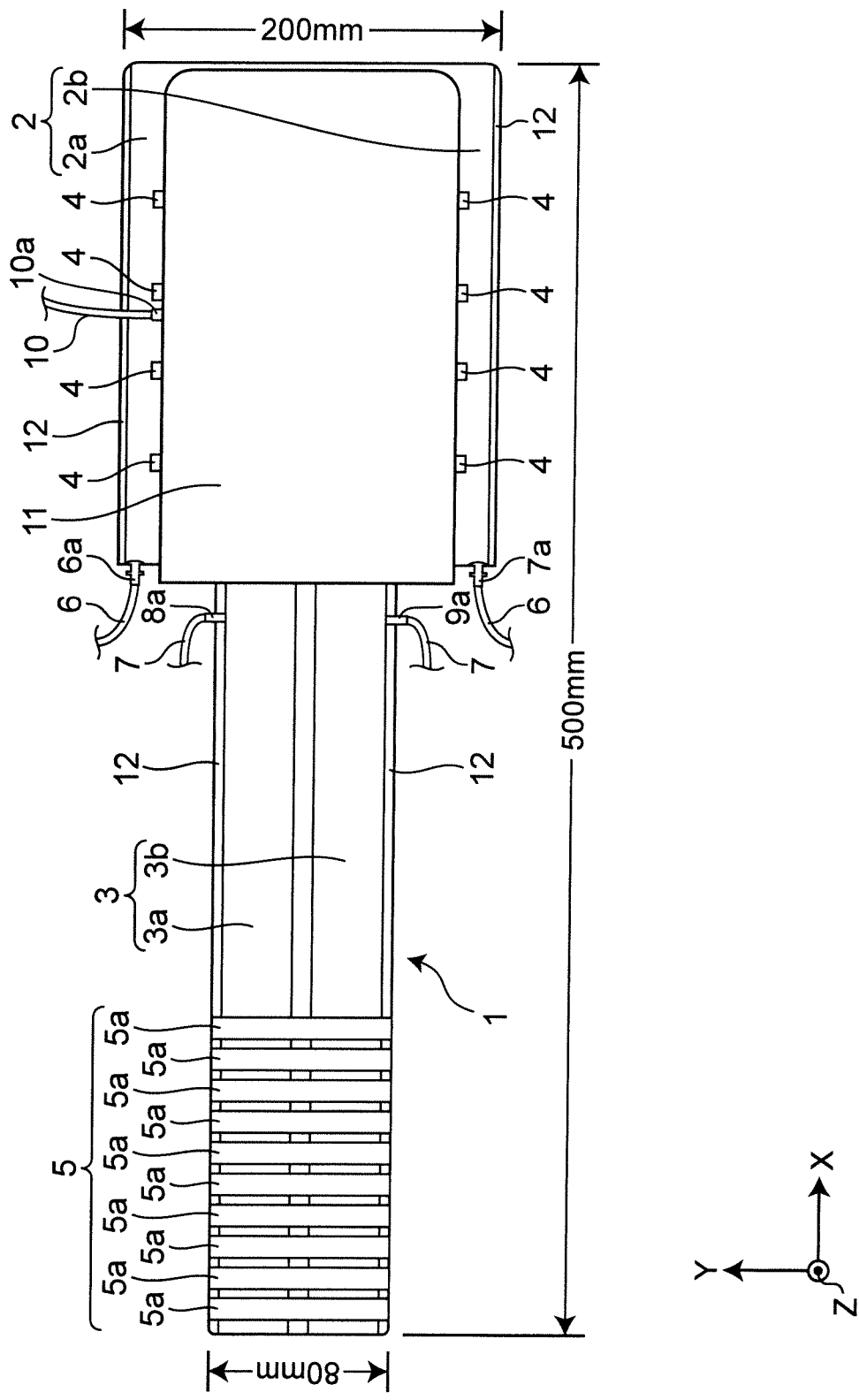
FIG. 1 is a top view illustrating an appearance of a blood pressure measuring cuff according to a first embodiment of the present invention.

Hereinafter, embodiments of the present invention will be described with reference to the drawings. In each of the following embodiments, the same components are designated by the same reference numerals, and the description thereof will be omitted.

First Embodiment

Figure 2:
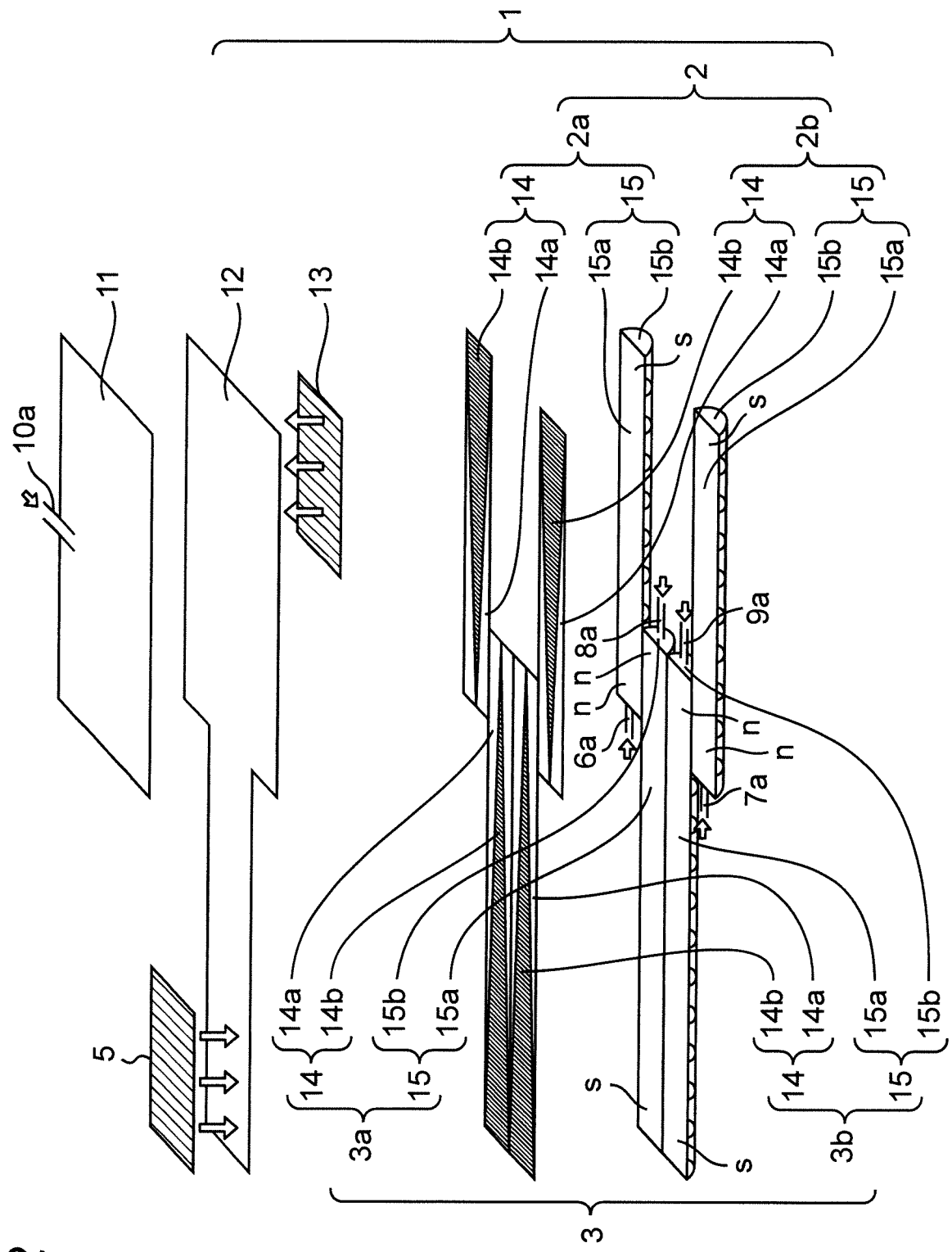
FIG. 2 is an exploded perspective view illustrating a structure of the blood pressure measuring cuff in FIG. 1.

FIG. 1 is a top view illustrating an appearance of a blood pressure measuring cuff according to a first embodiment of the present invention, and FIG. 2 is an exploded perspective view illustrating a structure of the blood pressure measuring cuff in FIG. 1. The blood pressure measuring cuff in FIG. 1 includes a measurement air bag 11 used to measure a blood pressure and a soft gripper 1. The soft gripper 1 includes an elongated first actuator 2 deformed by receiving supply of fluid, an elongated second actuator 3 deformed by receiving supply of fluid, a base plastic film 12 welding the first actuator 2 and the second actuator 3, and a Hook-and-Loop fastener 4 that detachably attaches the measurement air bag 11.

In FIGS. 1 and 2, the first actuator 2 includes a first bending type actuator unit 2a and a second bending type actuator unit 2b, in each of which the fluid can be stored. The second actuator 3 includes a first bending type actuator unit 3a and a second bending type actuator unit 3b, in each of which the fluid can be stored. The first actuator 2 and the second actuator 3 extend from bases n toward opposite sides to each other. When receiving the supply of the fluid, each of the first and second actuators 2, 3 sequentially surrounds an object from the base n toward a side of leading end s of the each of the first and second actuators 2, 3. When the soft gripper 1 is detached from the object, the fluid is exhausted from the first and second actuators 2, 3 to which the fluid was supplied. Consequently, bending states of the first and second actuators 2, 3 surrounding the object in a curved manner are eliminated, and the first and second actuators 2, 3 are detached from the object.

In the first embodiment, with respect to a width direction perpendicular to a longitudinal direction in which the first and second actuators 2, 3 extend, one of the sides of the leading ends s of the first and second actuators 2, 3 is divided into two portions, and the other side of the leading end s of the first and second actuators 2, 3 is disposed between the two divided portions. With this configuration, the soft gripper can wind around the object without a gap when surrounding the object.

Since the measurement air bag 11 needs to be changed according to a human arm diameter after being wound around an upper arm 90, the measurement air bag 11 is detachable using the Hook-and-Loop fastener 4. An air supply port 10a is provided in the measurement air bag 11 such that the fluid can be supplied and discharged. For example, gas such as air is used as the fluid. However, the fluid is not limited to the air, but liquid such as water may be used. The fluid is supplied from a hydraulic pump (see FIG. 5) that is of a fluid supply source to the measurement air bag 11 through a tube 10 connected to the air supply port 10a, and discharged from the measurement air bag 11 through the tube 10.

A plurality of strip-shaped Hook-and-Loop fasteners are stuck to a front surface side and a back surface side of the base plastic film 12. In particular, on the side of the first actuator 2, a fixing element such as a Hook-and-Loop fastener 13 is stuck onto a back surface side of the base plastic film 12. That is, the fixing element is provided on an outer periphery of a leading end side of the first actuator 2. On the side of the second actuator 3, a fixing element such as a Hook-and-Loop fastener 5 in which a plurality of strip-shaped Hook-and-Loop fasteners 5a are arranged is stuck onto a front surface side of the base plastic film 12. That is, the fixing element is provided on an inner periphery of the leading end s of the second actuator 3. When the soft gripper 1 wraps the upper arm 90, the Hook-and-Loop fastener 13 and the Hook-and-Loop fastener 5 are stuck while overlapping each other, and the soft gripper 1 is fixed to the upper arm 90.

Each of the first bending type actuator units 2a, 2b and the second bending type actuator units 3a, 3b includes a flexible plate 14 and a fluid bag 15, which is stuck to the flexible plate 14 and can store the fluid therein. For example, the flexible plate 14 is made of low density polyethylene (LDPE) or polypropylene (PP). In the first embodiment, the flexible plate 14 is made of vinyl chloride. The flexible plate 14 is constructed with two plates of a first vinyl chloride plate 14a having a rectangular shape in an XY planar view and a triangular second vinyl chloride plate 14b bonded on the first vinyl chloride plate 14a. Each of the first vinyl chloride plate 14a and the second vinyl chloride plate 14b has a thickness of 0.2 mm.

The fluid bag 15 has a bag structure constructed with a first sheet member 15a and a second sheet member 15b. Since the second sheet member 15b is subjected to a folding process called a pleat, when an air pressure is applied to the bag structure, a difference in surface area occurs to generate bending motion. Details of the fluid bag 15 will be described below with reference to FIGS. 3 and 4. Assuming that a length direction of each flexible plate 14 is an X-axis direction, that a width direction is a Y-axis direction, and that a thickness direction is a Z-axis direction, the soft gripper 1 has a length of approximately 500 mm in the X-axis direction, the first actuator 2 has a width of approximately 200 mm in the Y-axis direction, and the second actuator 3 has a width of approximately 80 mm in the Y-axis direction.

Air supply ports 6a, 7a, 8a, 9a are provided in the fluid bags 15 of the first bending type actuator units 2a, 2b and the second bending type actuator units 3a, 3b, respectively, such that the fluid can be supplied to and discharged from each of the fluid bags 15. In the first embodiment, gas such as air is used as the fluid. However, the fluid is not limited to the air, but liquid such as water may be used. The fluid is supplied from the hydraulic pump (see FIG. 5) that is of the fluid supply source to the fluid bags 15 connected to the air supply ports 6a, 7a, 8a, 9a through the tubes 6, 7. For example, after the fluid is simultaneously supplied to the first bending type actuator units 2a, 2b from an outside such as the hydraulic pump through the air supply ports 6a, 7a to pressurize the first actuator 2, the fluid is simultaneously supplied to the second bending type actuator units 3a, 3b through the air supply ports 8a, 9a to pressurize the second actuator 3. Consequently, it is possible to control timing at which the leading end s of the first actuator 2 is bent along an outer peripheral surface of the object and timing at which the leading end s of the second actuator 3 is bent along an outer peripheral surface of the object. For example, the first actuator 2 is sequentially bent from the side of the base n toward the side of the leading end s, and then the second actuator 3 is sequentially bent from the side of the base n toward the side of the leading end s.

Figure 3:
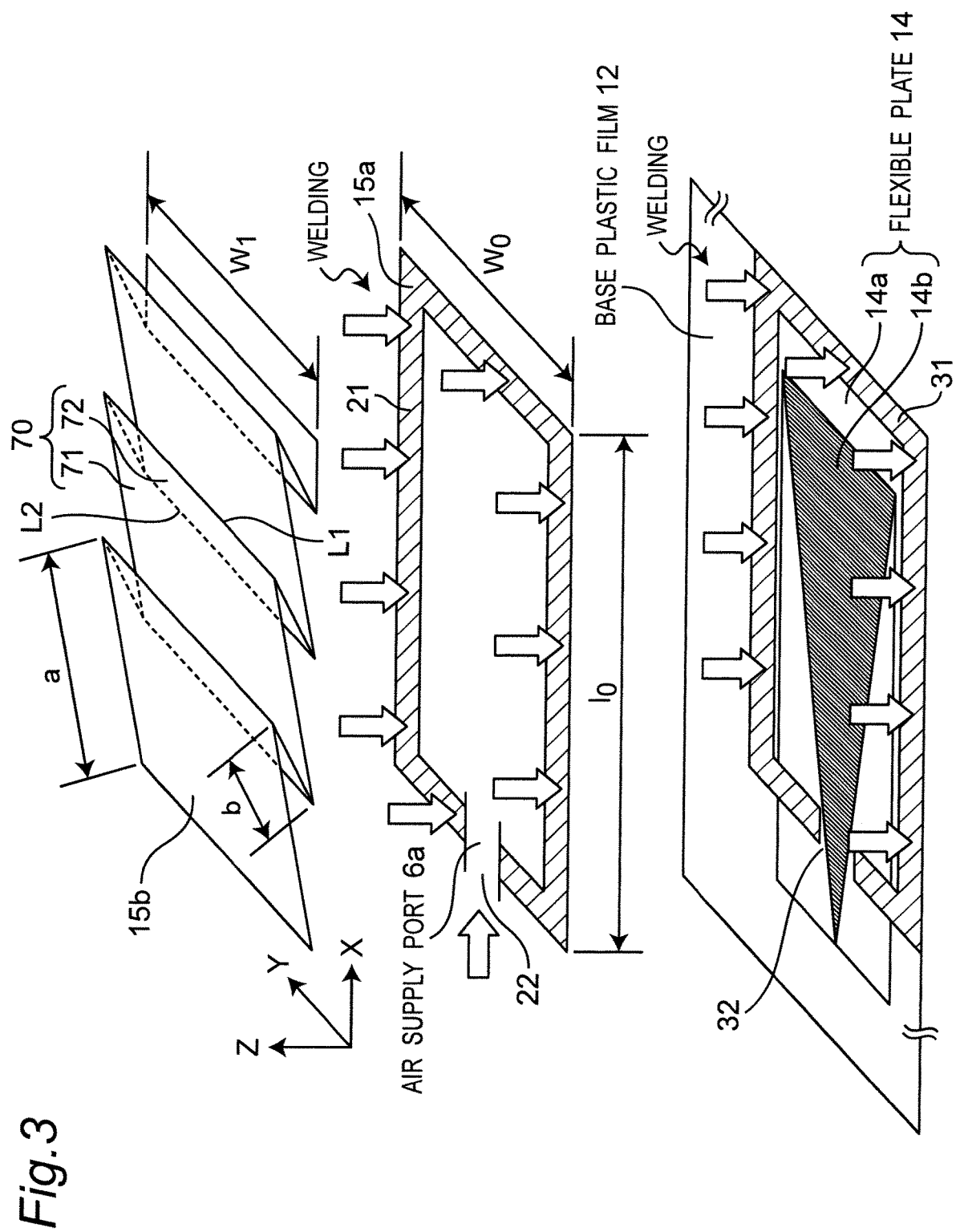
FIG. 3 is a schematic perspective view illustrating a fluid bag 15 in FIG. 2.

FIG. 3 is a schematic perspective view illustrating the fluid bag 15 in FIG. 2. As illustrated in FIG. 3, each of the first sheet member 15a and the second sheet member 15b is constructed with a sheet member having a substantially rectangular shape in the XY planar view, a dimension in the length direction (X-axis direction) of the second sheet member 15b is longer than a dimension $l_0$ in the length direction of the first sheet member 15a, and a dimension W1 in the width direction (Y-axis direction) of the second sheet member 15b is longer than a dimension W0 in the width direction of the first sheet member 15a. At this point, it is assumed that the length directions of the first sheet member 15a and the second sheet member 15b are the X-axis direction, that the width directions of the first sheet member 15a and the second sheet member 15b are the Y-axis direction, and that the thickness directions of the first sheet member 15a and the second sheet member 15b are the Z-axis direction.

As illustrated in FIG. 3, the second sheet member 15b is divided in the length direction to form a plurality of expandable pleats 70, and each of the pleat 70 includes an outside pleat 71 located outside and an inside pleat 72 folded inside. The outside pleat 71 and the inside pleat 72 are formed by being folded back at a pleat folding line L1 constituting a mountain of the pleat 70 and a pleat folding line L2 constituting a valley. The pleat folding line L1 and the pleat folding line L2 are provided such that a dimension a in the length direction of the outside pleat 71 is longer than a dimension b in the length direction of the inside pleat 72 when the pleat 70 is formed.

When a bag structure is formed using the first sheet member 15a and the second sheet member 15b having different surface areas, in order to form a space (fluid chamber) in which the fluid is stored, the first sheet member 15a and the second sheet member 15b are thermally welded while a corner of the second sheet member 15b is aligned with a corner (welded portion) 21 of the first sheet member 15a indicated by hatching in FIG. 3. At this point, a portion where the dimension a in the length direction of the outside pleat 71 of the second sheet member 15b and the dimension b in the length direction of the inside pleat 72 overlap with each other is also thermally welded, the overlapping portion being aligned with the welded portion 21 of the first sheet member 15a. Consequently, the fluid can be prevented from leaking out of the fluid chamber to the outside. In FIG. 3, a non-welded portion 22 in which the first sheet member 15a and the second sheet member 15b are not thermally welded is provided in order to provide the air supply port 6a.

Then, the fluid bag 15 having the bag structure is thermally welded onto the base plastic film 12. In particular, the fluid bag 15 is thermally welded while aligned with a welded portion 31 of the base plastic film 12 indicated by hatching in FIG. 3. In FIG. 3, a non-welded portion 32 in which the base plastic film 12 and the fluid bag 15 are not thermally welded is provided in order to provide the air supply port 6a. The flexible plate 14 is assembled while inserted in a gap formed between the base plastic film 12 and the fluid bag 15.

Figure 4A:
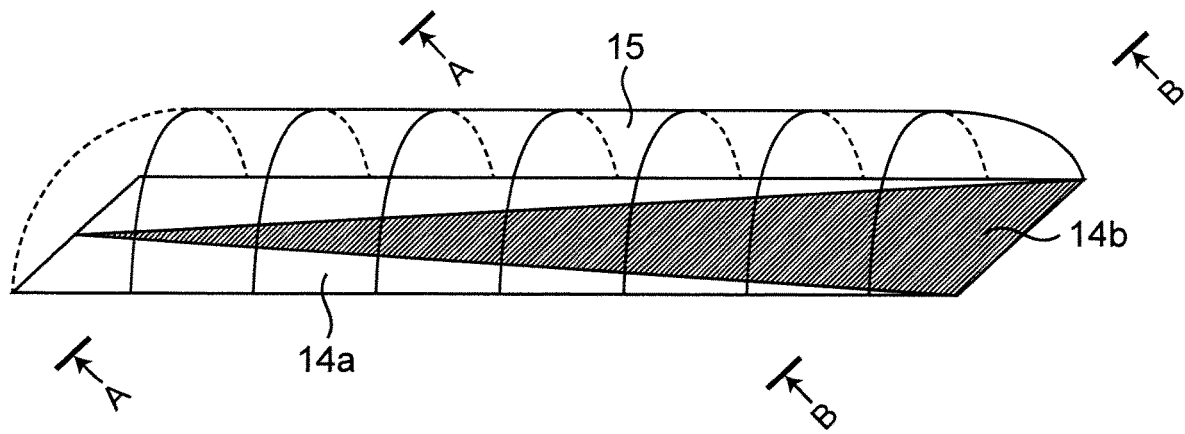
FIG. 4A is a perspective view illustrating a structure obtained by a combination of a flexible plate 14 and the fluid bag 15.
Figure 4B:
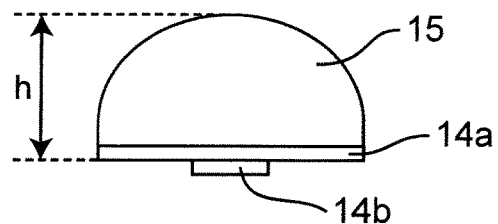
FIG. 4B is a longitudinal sectional view taken along line A-A in FIG. 4A.
Figure 4C:
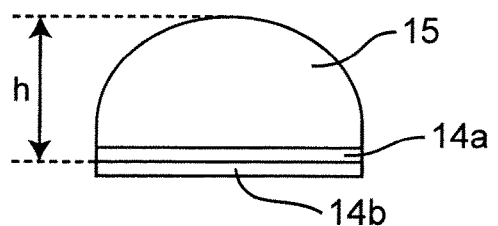
FIG. 4C is a longitudinal sectional view taken along line B-B in FIG. 4A.

FIG. 4A is a perspective view illustrating a structure obtained by a combination of the flexible plate 14 and the fluid bag 15, FIG. 4B is a longitudinal sectional view taken along line A-A in FIG. 4A, and FIG. 4C is a longitudinal sectional view taken along line B-B in FIG. 4A. In FIGS. 4A to 4C, the rectangular first vinyl chloride plate 14a is attached to prevent a change of a sectional shape of the fluid bag 15, thus preventing the change of the sectional shape and reducing a change in bending rigidity of the fluid bag 15 due to the sectional shape. The triangular second vinyl chloride plate 14b is attached to change the bending rigidity of the fluid bag 15. By setting the A-A side of the sectional view to the base (that is, setting the B-B side of the sectional view to the leading end), an amount of displacement per unit time is increased on the base side of the fluid bag 15, and the amount of displacement per unit time of the fluid bag 15 can be decreased sequentially toward the leading end side. That is, in the first and second actuators 2, 3, the bending rigidity on the side of the base n is smaller than that on the side of the leading end s. With this configuration, the sides of the bases n of the first and second actuators 2, 3 are bent along the outer peripheral surface of the object, and then the sides of the leading ends s are bent along the outer peripheral surface of the object. Thus, the same pressure is preferably applied to each of the first and second actuators 2, 3 without pressurizing the first and second actuators 2, 3 in the longitudinal direction a plurality of times. Consequently, pressurization control is easily performed when the first and second actuators 2, 3 are bent.

Operation of the soft gripper 1 having the above configuration will be described below.

Figure 5:
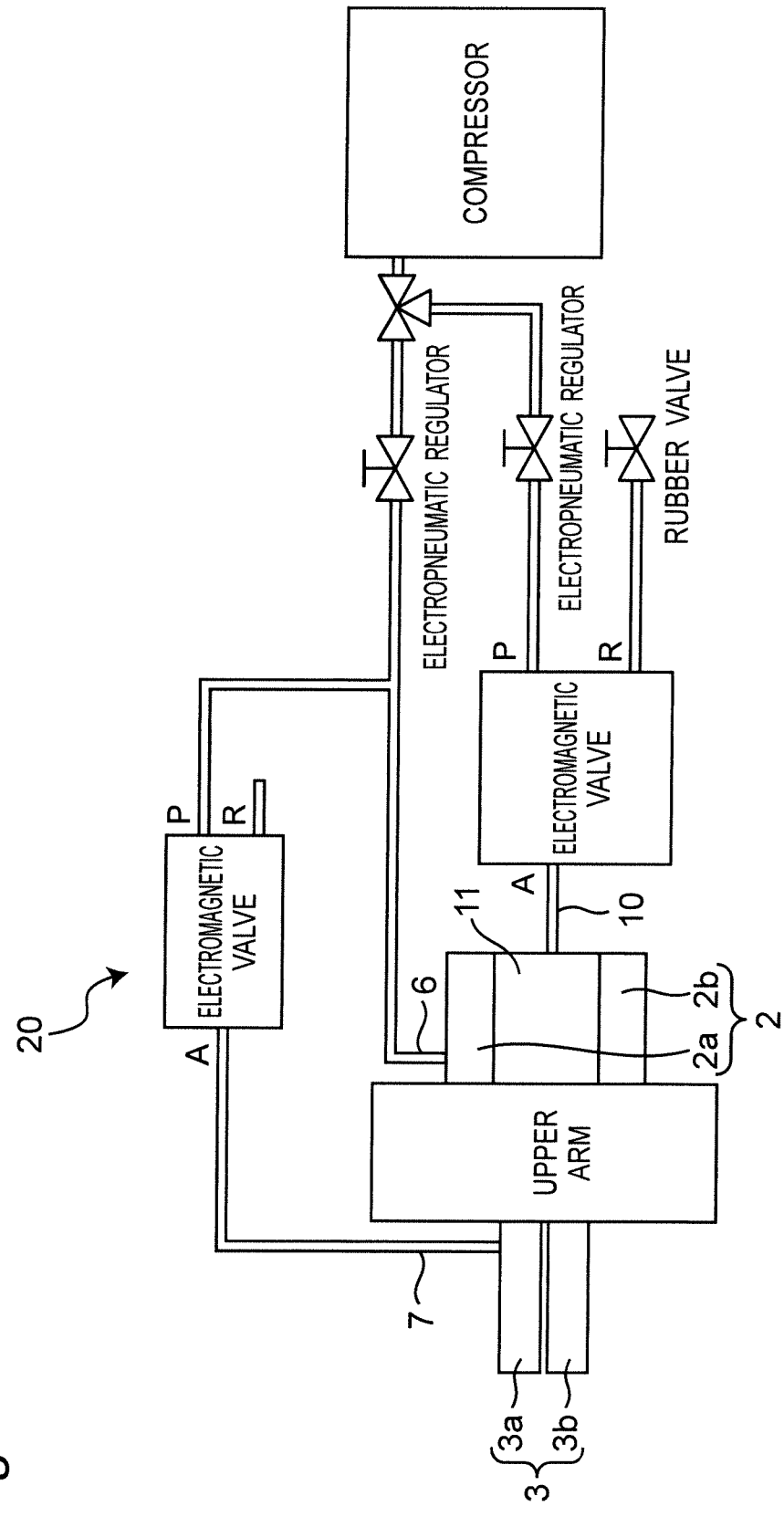
FIG. 5 is a schematic diagram illustrating a hydraulic pump 20 that supplies air as a fluid to the soft gripper 1 in FIG. 1.

FIG. 5 is a schematic diagram illustrating a hydraulic pump 20 that supplies the air as the fluid to the soft gripper 1 in FIG. 1. The hydraulic pump 20 includes a compressor that is of a pressure source, an electropneumatic regulator that adjusts an air pressure to a predetermined pressure value by controlling the air pressure using an electric signal, an electromagnetic valve, and a rubber valve. The hydraulic pump 20 can apply an electric signal corresponding to a predetermined pressure to the electropneumatic regulator through a computer, and obtain the air pressure adjusted to a target pressure value in a short time.

The operation of the soft gripper 1 when the pressures applied to the first and second actuators 2, 3 using the hydraulic pump 20 in FIG. 5 are set to 15 kPa will be described below.

Figure 6A:
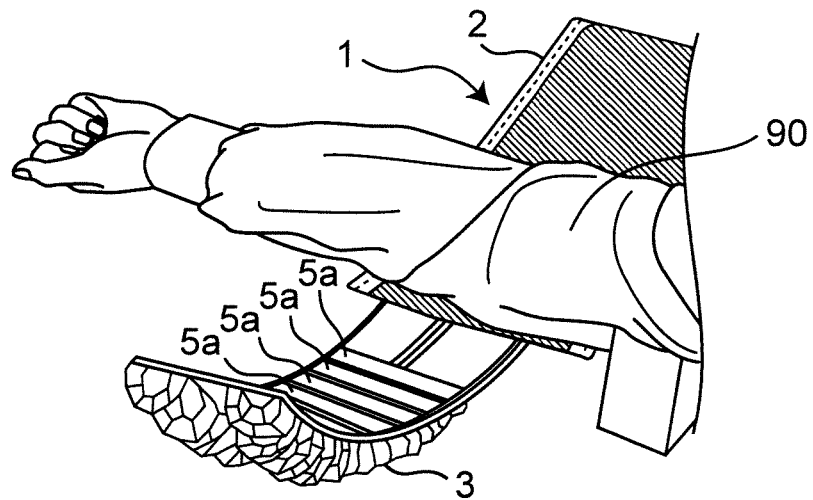
FIG. 6A is a schematic diagram illustrating a first state of operation of the soft gripper 1 in FIG. 1.
Figure 6B:
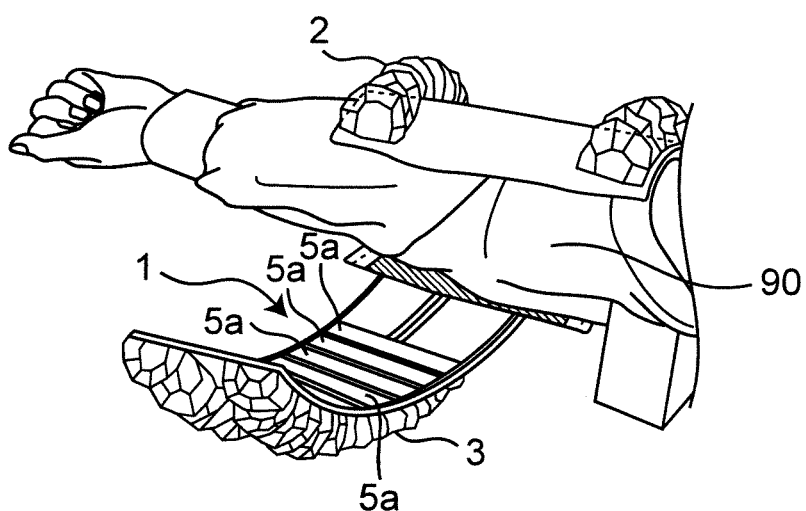
FIG. 6B is a schematic diagram illustrating a second state of the operation of the soft gripper 1 in FIG. 1.
Figure 6C:
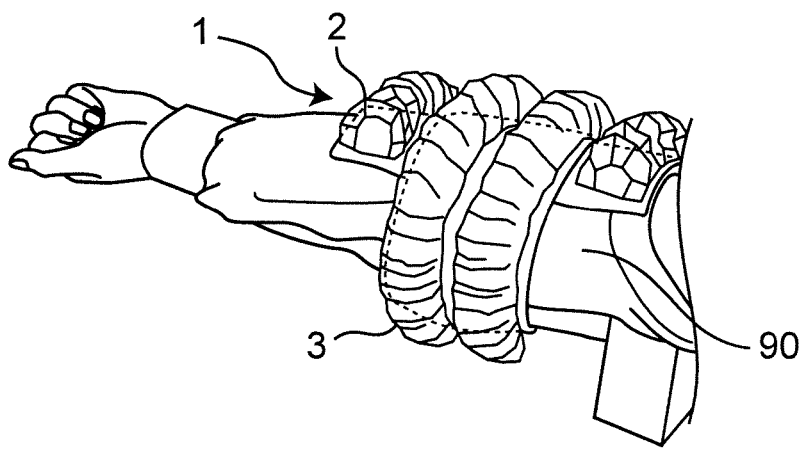
FIG. 6C is a schematic diagram illustrating a third state of the operation of the soft gripper 1 in FIG. 1.

FIGS. 6A to 6C are schematic diagrams illustrating the operation of the soft gripper 1 in FIG. 1. First, the upper arm 90 that is of the object is placed on the surface, on which the measurement air bag 11 is located, of the soft gripper 1 in the non-pressurized state (FIG. 6A). Then, when a pressure of 15 kPa is applied only to the first actuator 2, the first actuator 2 winds around the upper arm 90 (FIG. 6B). When a pressure of 15 kPa is also applied to the second actuator 3 after the first actuator 2 winds around the upper arm 90, the second actuator 3 winds around the upper arm 90 (FIG. 6C). Thus, the soft gripper 1 can wind around the upper arm 90. This will be described in more detail below.

Figure 7:
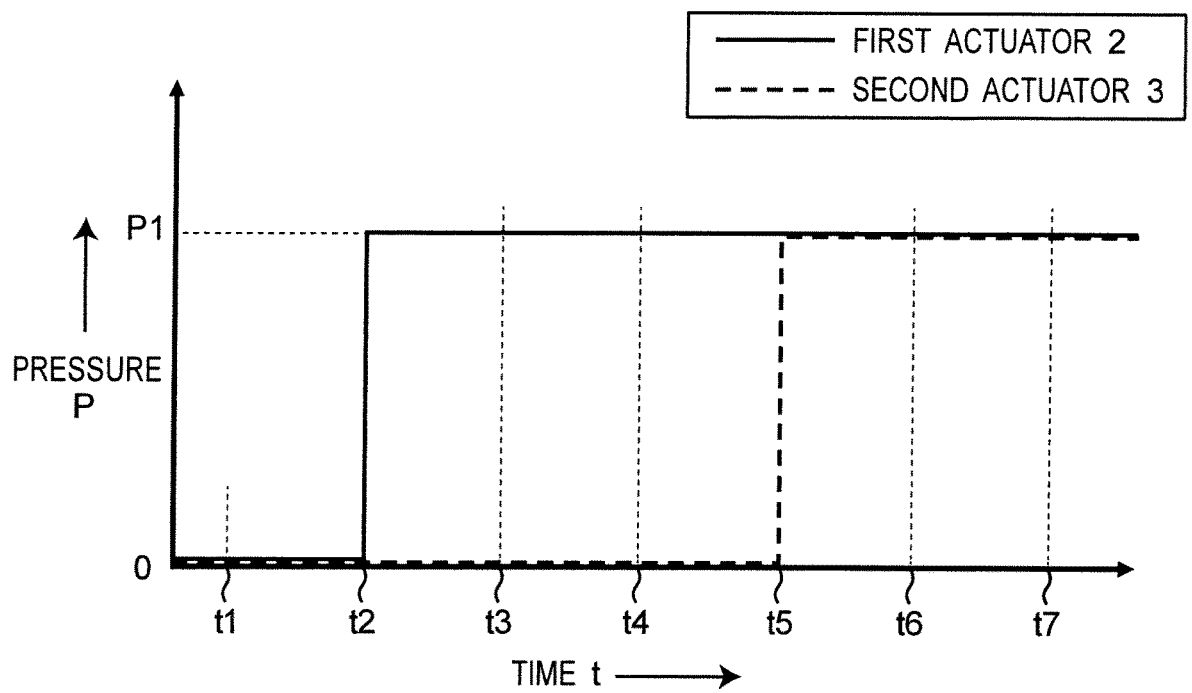
FIG. 7 is a time axis waveform chart illustrating a change in pressure P to time t, the pressure P being applied to a first actuator 2 and a second actuator 3 in FIG. 1.
Figure 8A:
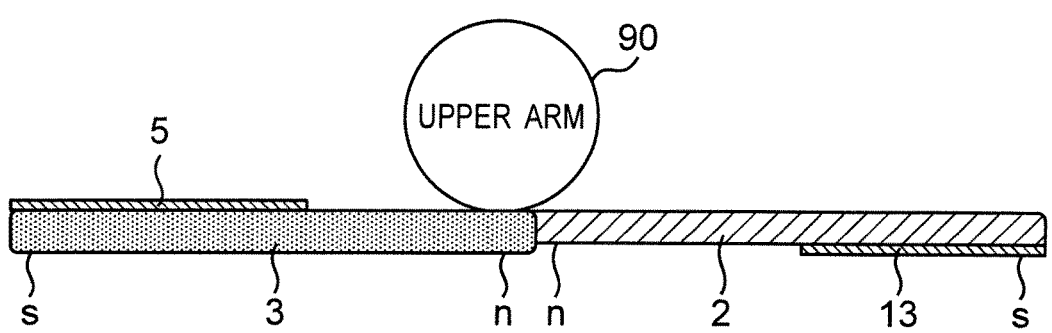
FIG. 8A is a schematic diagram illustrating operating states of the first actuator 2 and the second actuator 3 at time t1 in FIG. 7.
Figure 8B:
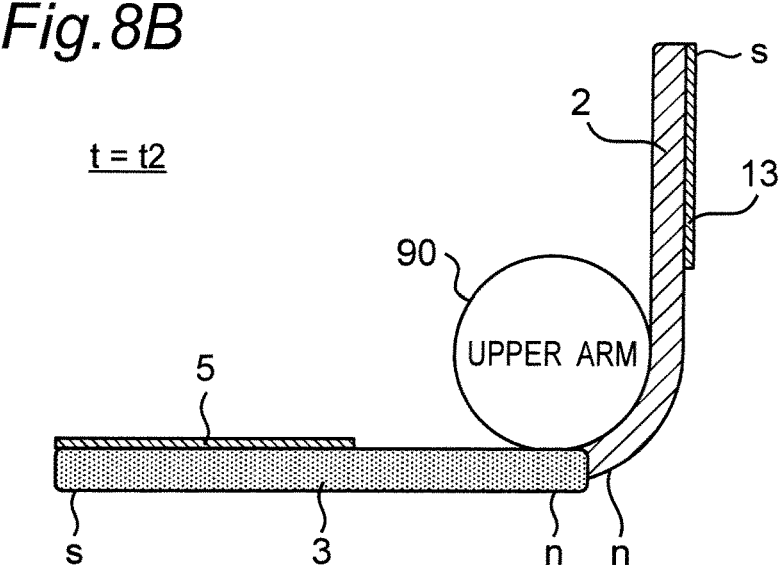
FIG. 8B is a schematic diagram illustrating the operating states of the first actuator 2 and the second actuator 3 at time t2 in FIG. 7.
Figure 8C:
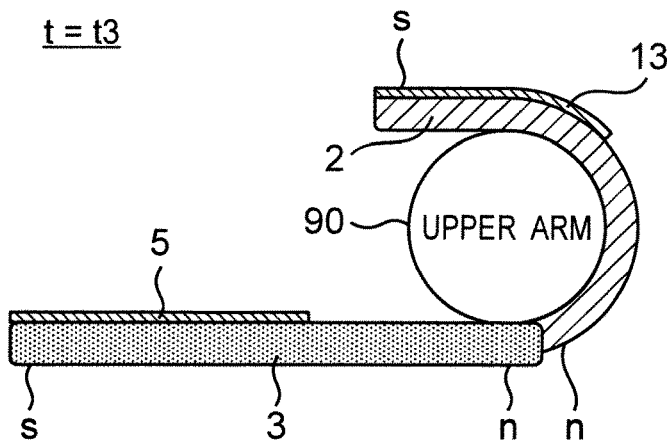
FIG. 8C is a schematic diagram illustrating the operating states of the first actuator 2 and the second actuator 3 at time t3 in FIG. 7.
Figure 8D:
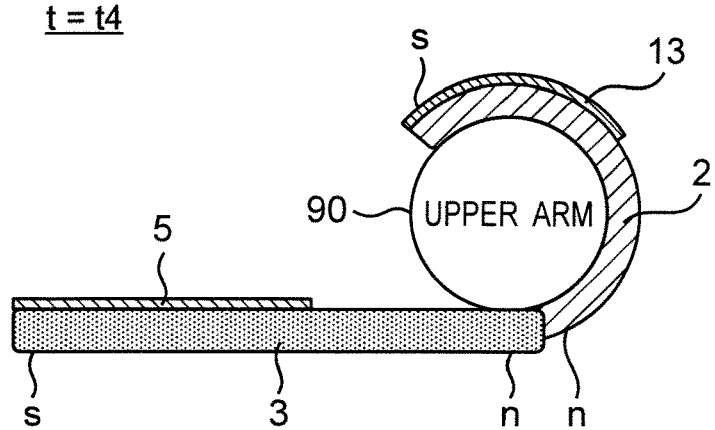
FIG. 8D is a schematic diagram illustrating the operating states of the first actuator 2 and the second actuator 3 at time t4 in FIG. 7.
Figure 8E:
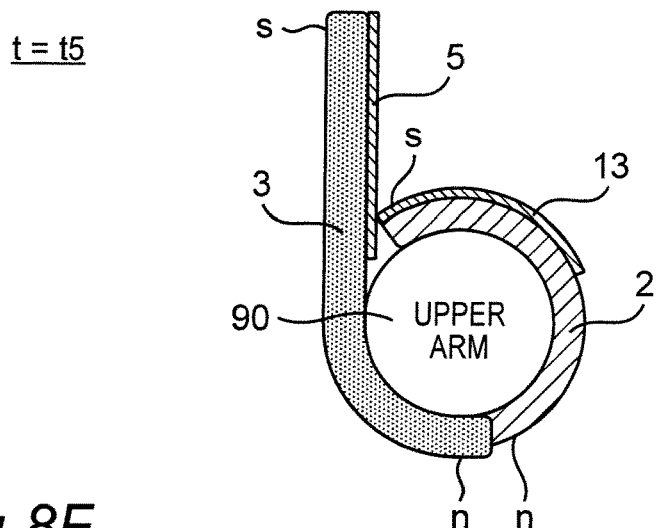
FIG. 8E is a schematic diagram illustrating the operating states of the first actuator 2 and the second actuator 3 at time t5 in FIG. 7.
Figure 8F:
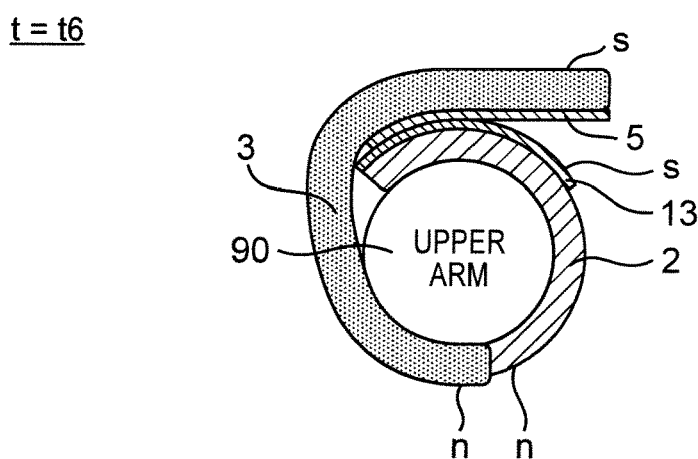
FIG. 8F is a schematic diagram illustrating the operating states of the first actuator 2 and the second actuator 3 at time t6 in FIG. 7.
Figure 8G:
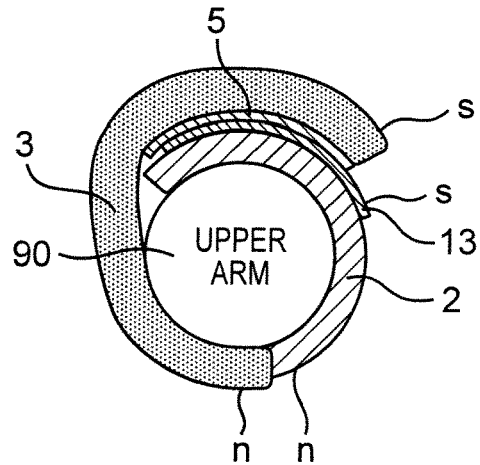
FIG. 8G is a schematic diagram illustrating the operating states of the first actuator 2 and the second actuator 3 at time t7 in FIG. 7.

FIG. 7 is a time axis waveform chart illustrating a change in pressure P to time t, the pressure P being applied to the first and second actuators 2, 3 in FIG. 1, and FIGS. 8A to 8G are schematic diagrams illustrating operating states of the first and second actuators 2, 3 at each time t in FIG. 7.

In FIGS. 7 and 8, the pressures applied to the first and second actuator 2, 3 are set to zero at time t1 (non-pressurized). At this point, the upper arm 90 is placed on the surface of the measurement air bag 11 of the soft gripper 1 (identical to FIG. 6A). At time t2, a pressure P1 is applied only to the first actuator 2 (the second actuator 3 remains in the non-pressurized state). At this point, the side of the base n of the first actuator 2 starts to be bent along the outer peripheral surface of the upper arm 90. The state in which the pressure P1 is applied only to the first actuator 2 is continued (the second actuator 3 remains in the non-pressurized state), and at time t3, the leading end side of the first actuator 2 is bent along the outer peripheral surface of the upper arm 90 subsequent to the base side.

The state in which the pressure P1 is applied only to the first actuator 2 is further continued, and at time t4, the leading end side of the first actuator 2 is further bent along the outer peripheral surface of the upper arm 90 to wrap the upper arm 90 (identical to FIG. 6B). At time t5, the pressure P1 is also applied to the second actuator 3 while the pressure P 1 is applied to the first actuator 2. At this point, the side of the base n of the second actuator 3 starts to be bent along the outer peripheral surface of the upper arm 90. The state in which the pressure P1 is applied to the first and second actuators 2, 3 is continued, and at time t6, the leading end side of the second actuator 3 is bent along the outer peripheral surface of the upper arm 90 subsequent to the base side. The state is continued, and at time t7, the leading end side of the second actuator 3 is further bent along the outer peripheral surface of the upper arm 90 to wrap the upper arm 90 (identical to FIG. 6C).

Figure 9:
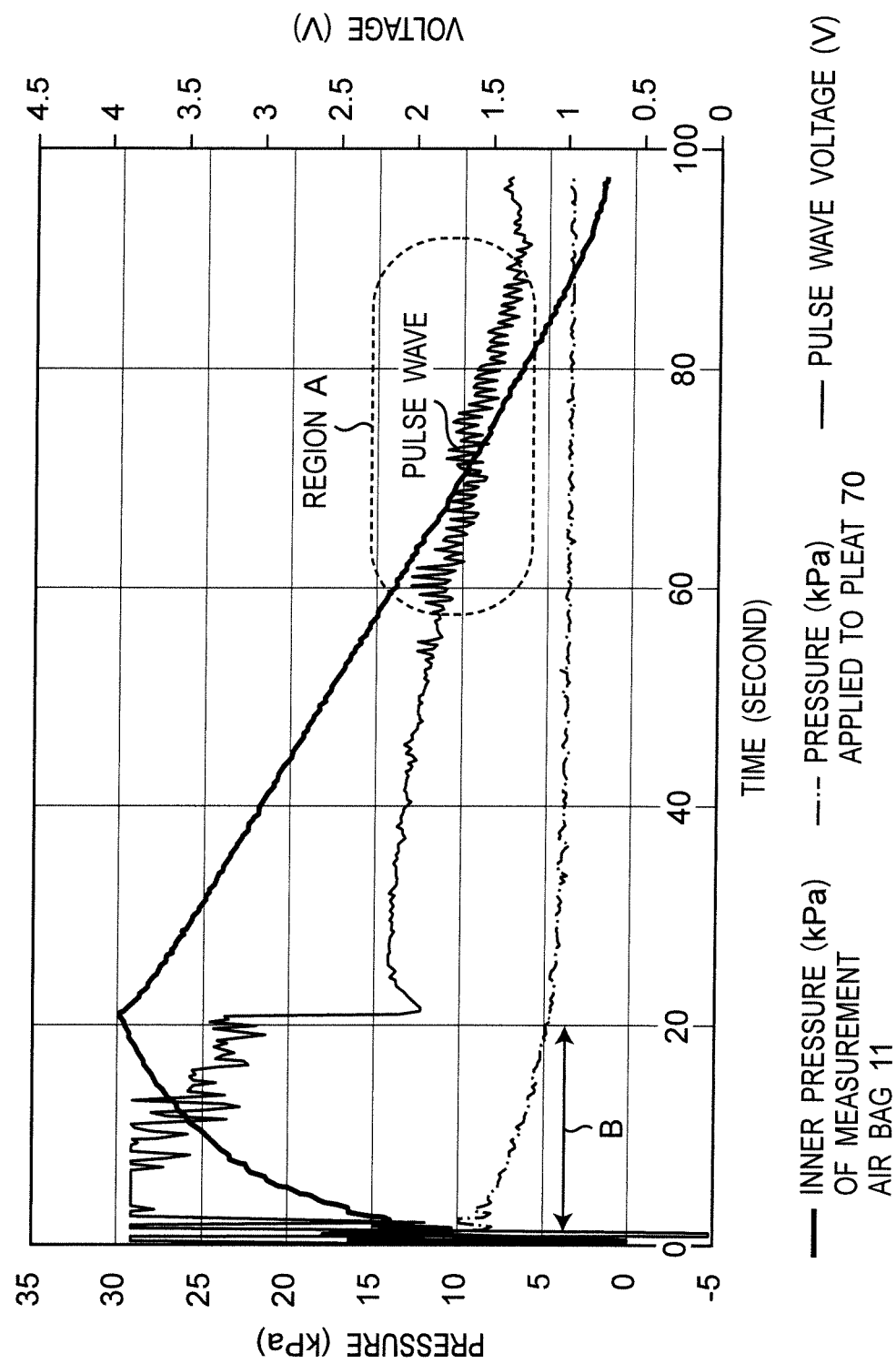
FIG. 9 is a graph illustrating detection of a pulse wave using a measurement air bag 11 of the soft gripper 1 in FIG. 1.

FIG. 9 is a graph illustrating detection of a pulse wave using the blood pressure measuring cuff in FIG. 1. As can be seen from FIG. 9, in the graph of the pulse wave voltage, a peak indicating a pulse wave appears continuously in a region A of around 60 seconds to around 90 seconds, and the blood pressure can be measured based on the peaks. Therefore, it can be understood that the soft gripper 1 can be used as the blood pressure measuring cuff. Although the pressure applied to the pleat 70 is decreased in a section B, this is caused by a leakage of a valve or the like, and the pressure becomes constant after a certain time elapses.

First Modification

Figure 25A:
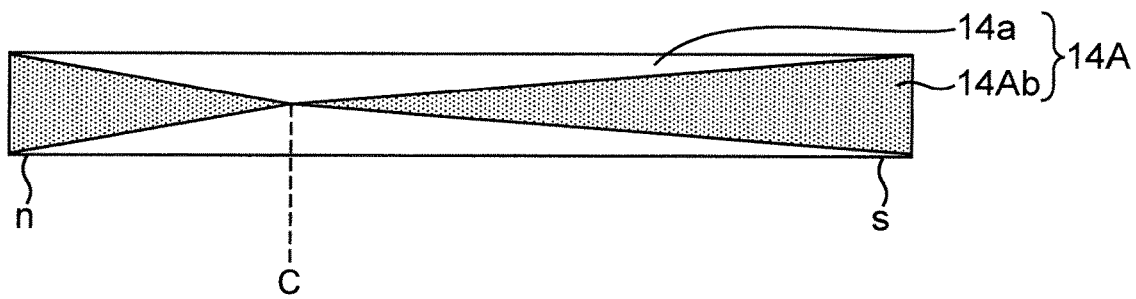
FIG. 25A is a top view illustrating a flexible plate 14A according to a first modification of the first embodiment of the present invention.

FIG. 25A is a top view illustrating a flexible plate 14A according to a first modification of the first embodiment of the present invention. The flexible plate 14A in FIG. 25A is different from the flexible plate 14 in FIG. 2 in that two triangular second vinyl chloride plates 14Ab are bonded onto the first vinyl chloride plate 14a having the rectangular shape in the XY planar view instead of the triangular second vinyl chloride plate 14b bonded onto the first vinyl chloride plate 14a. The two second vinyl chloride plates 14Ab are disposed such that apexes of the triangles are matched with each other at a specific point C between the base n and the leading end s of the flexible plate 14A. With this configuration, when receiving the supply of the fluid, the first and second actuators 2, 3 can sequentially surround the upper arm 90 from the specific point C toward the side of the leading end s and from the specific point C toward the side of the base n.

Second Modification

Figure 25B:
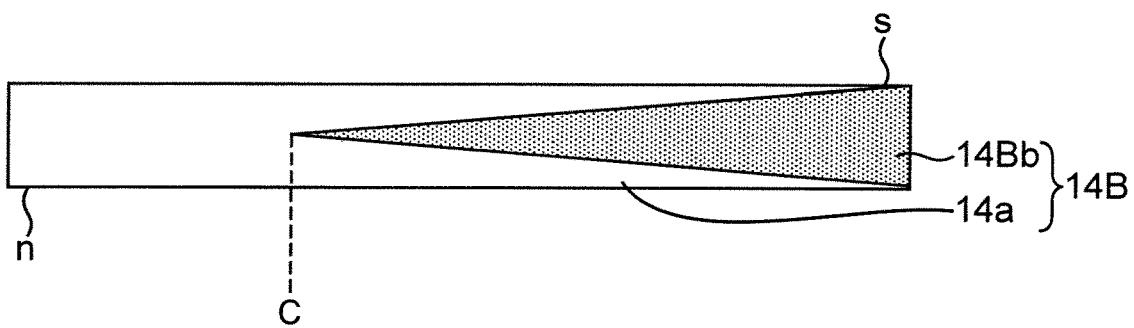
FIG. 25B is a top view illustrating a flexible plate 14B according to a second modification of the first embodiment of the present invention.

FIG. 25B is a top view illustrating a flexible plate 14B according to a second modification of the first embodiment of the present invention. The flexible plate 14B in FIG. 25B is different from the flexible plate 14 in FIG. 2 in that a triangular second vinyl chloride plate 14Bb is bonded onto the first vinyl chloride plate 14a having the rectangular shape in the XY planar view instead of the triangular second vinyl chloride plate 14b bonded onto the first vinyl chloride plate 14a. In the second vinyl chloride plate 14Bb, the apex of the triangular second vinyl chloride 14Ab is disposed at the specific point C between the base n and the leading end s of the flexible plate 14B. With this configuration, when receiving the fluid supply, the first and second actuators 2, 3 can sequentially surround the upper arm 90 from the specific point C toward the side of the leading end s.

Third Modification

Figure 26:
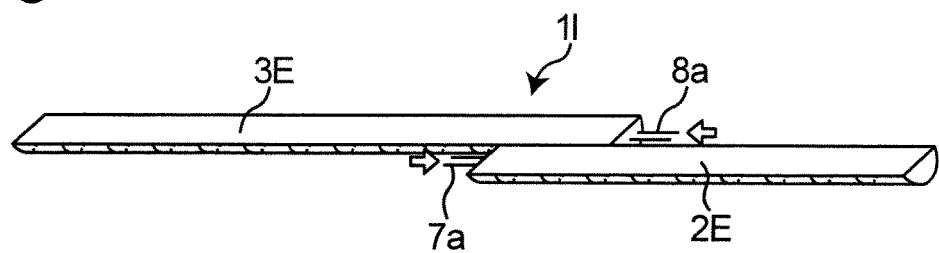
FIG. 26 is a perspective view schematically illustrating a configuration of a soft gripper 1I according to a third modification of the first embodiment of the present invention.

FIG. 26 is a perspective view schematically illustrating a configuration of a soft gripper 1I according to a third modification of the first embodiment of the present invention. The soft gripper 1I in FIG. 26 is different from the soft gripper 1 in FIG. 2 in that the side of the leading end s is not divided with respect to the width direction perpendicular to the longitudinal direction in which first and second actuators 2E, 3E extend.

An air supply port 7a that supplies and discharges the fluid to and from the fluid bag of the first actuator 2E constituting the soft gripper 1I, and an air supply port 8a that supplies and discharges the fluid to and from the fluid bag of the second actuator 3E constituting the soft gripper 1I are provided in the soft gripper 1I of FIG. 26.

Even in this case, when receiving the fluid supply, the first and second actuators 2E, 3E can sequentially surround the object from the side of the base n toward the side of the leading end s.

Fourth Modification

Figure 27:
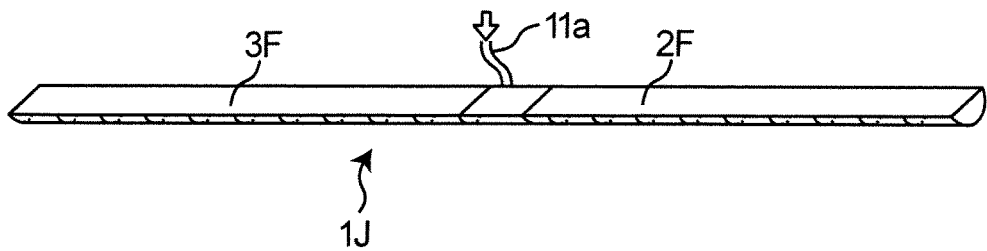
FIG. 27 is a perspective view schematically illustrating a configuration of a soft gripper 1J according to a fourth modification of the first embodiment of the present invention.

FIG. 27 is a perspective view schematically illustrating a configuration of a soft gripper 1J according to a fourth modification of the first embodiment of the present invention. The soft gripper 1J in FIG. 27 is different from the soft gripper 1I in FIG. 26 in that one air supply port capable of supplying and discharging the fluid to and from each fluid bag is provided. In particular, the air supply port 7a that supplies and discharges the fluid to and from the fluid bag of the first actuator 2E constituting the soft gripper 1I, and the air supply port 8a that supplies and discharges the fluid to and from the fluid bag of the second actuator 3E constituting the soft gripper 1I are provided in the soft gripper 1I of FIG. 26. On the other hand, one air supply port 11a that supplies and discharges the fluid to and from the fluid bags of the first and second actuators 2F, 3F constituting the soft gripper 1J in FIG. 27 is provided in the soft gripper 1J of FIG. 27.

Fifth Modification

Figure 28A:
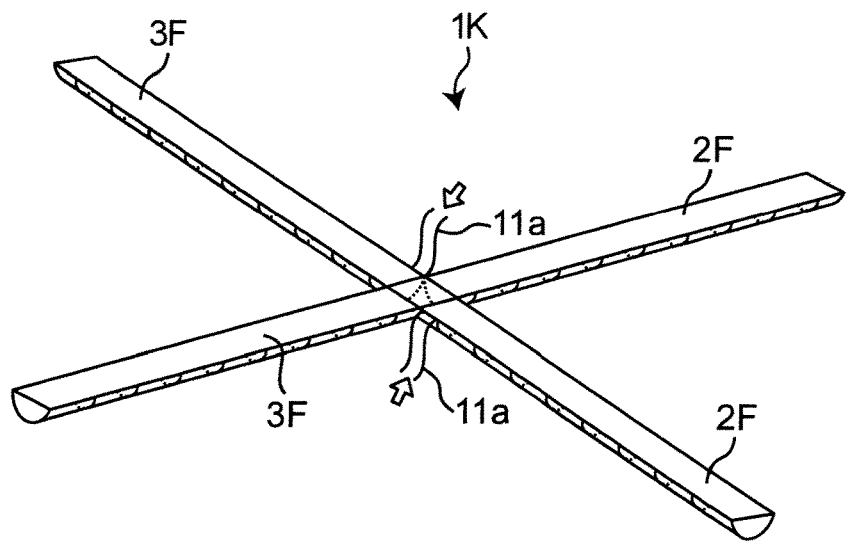
FIG. 28A is a perspective view schematically illustrating a configuration of a soft gripper 1K according to a fifth modification of the first embodiment of the present invention.

FIG. 28A is a perspective view schematically illustrating a configuration of a soft gripper 1K according to a fifth modification of the first embodiment of the present invention. The soft gripper 1K in FIG. 28A is configured such that two soft grippers 1J in FIG. 27 are disposed into a substantially cross shape. The Hook-and-Loop fastener is provided on the outer periphery at the leading end of the first actuator, the Hook-and-Loop fastener is provided on the inner periphery at the leading end of the second actuator, and a sphere 92 is surrounded by first and second actuators 2F, 3F. At this point, the Hook-and-Loop fasteners may be fixed while overlapping each other.

Figure 28B:
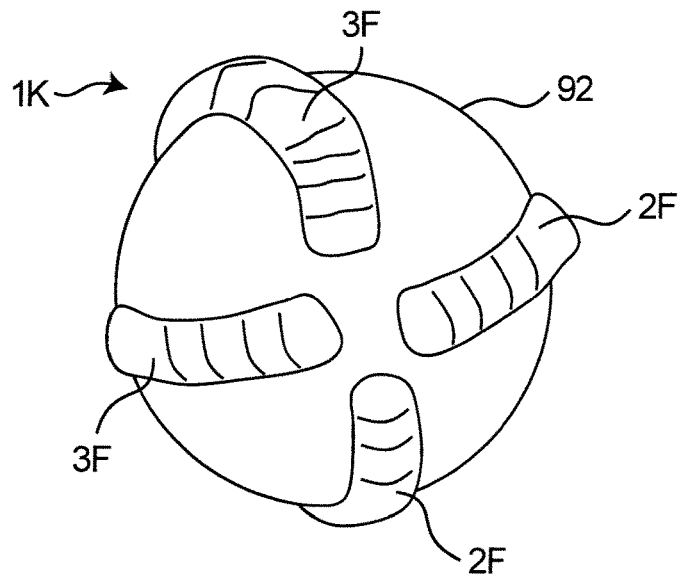
FIG. 28B is a schematic view illustrating the operation of the soft gripper 1K in FIG. 28A.

FIG. 28B is a schematic diagram illustrating the operation of the soft gripper 1K in FIG. 28A. As illustrated in FIG. 28B, when the fluid is supplied from each air supply port 11a, the fluid is supplied to the fluid bags of the first and second actuators 2F, 3F, and the first and second actuators 2F, 3F are bent along the outer peripheral surface of the sphere 92 to wrap the sphere 92.

Each of the actuators of the second to fifth modifications may be constructed with a fluid bag 15A according to a third embodiment (to be described later). In that case, the flexible plate 14 may be eliminated. Additionally, the configurations of an opening air bag 30 and a stretching air bag 40 according to a second embodiment (to be described later) may be incorporated.

Second Embodiment

Figure 10:
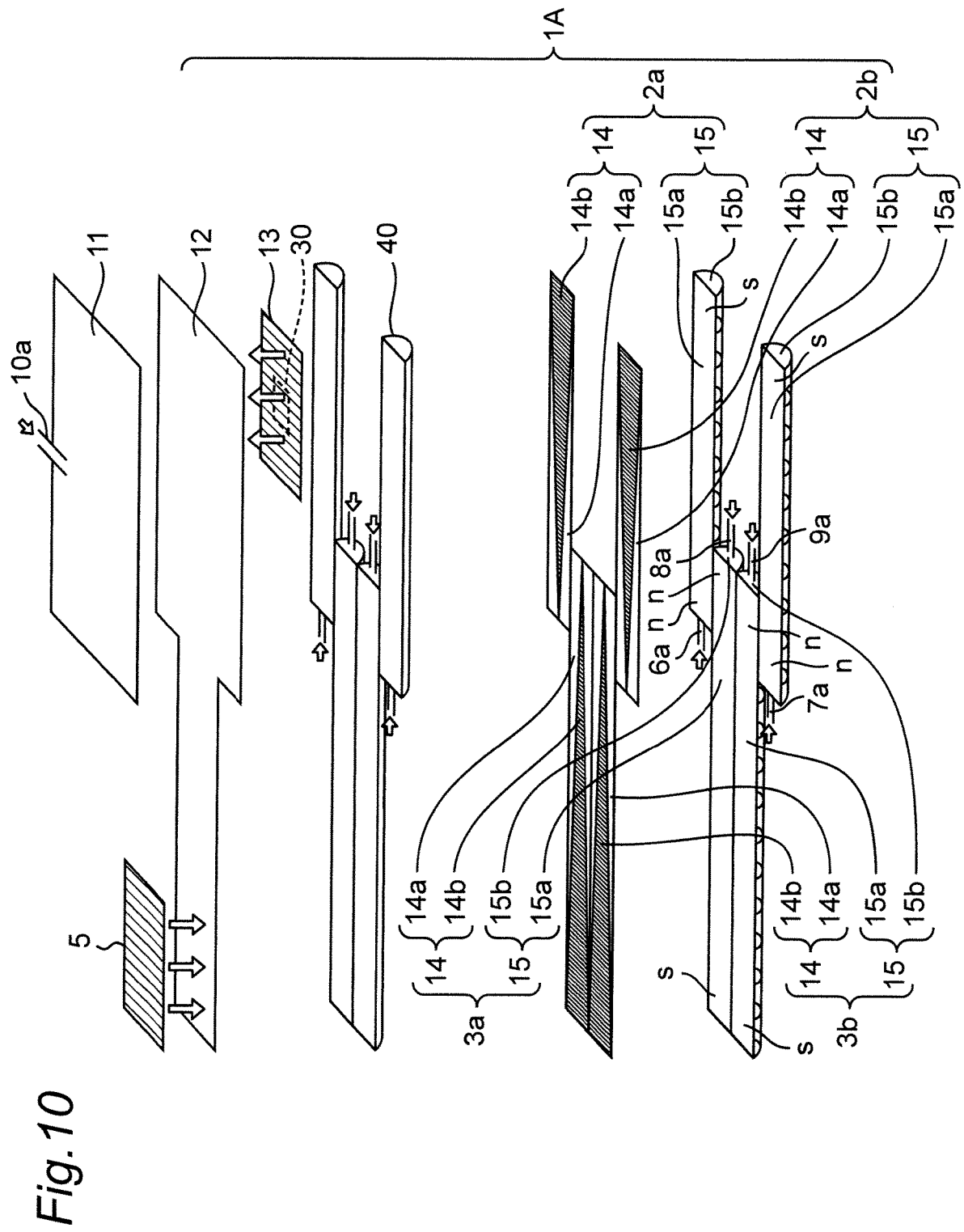
FIG. 10 is an exploded perspective view illustrating a structure of a soft gripper 1A according to a second embodiment.

FIG. 10 is an exploded perspective view illustrating a structure of a soft gripper 1A according to the second embodiment. The soft gripper 1A in FIG. 10 is different from the soft gripper 1 in FIG. 2 in that the opening air bag 30 is attached onto the Hook-and-Loop fastener 13, and that the stretching air bag 40 is attached between the base plastic film 12 and the flexible plate 14. That is, in the second embodiment, the opening air bag 30 that is of a detaching fluid bag, in which the fluid is supplied from the outside to detach these Hook-and-Loop fasteners 5, 13 from each other, is disposed at the positions corresponding to the Hook-and-Loop fasteners 5, 13. The stretching air bag 40, which is of a stretching fluid bag in which the fluid is supplied from the outside to eliminate and stretch the bending of the first and second actuators 2, 3, is provided along each surface side, which comes into contact with the upper arm 90, of the first and second actuators 2, 3.

At this point, the fixing between the Hook-and-Loop fastener 5 and the Hook-and-Loop fastener 13 is automatically released by supplying, for example, air as the fluid from the hydraulic pump 20 to the opening air bag 30. With this configuration, the fixing between the first and second actuators 2, 3 can automatically be released.

Stretching speeds of the first and second actuators 2, 3 can be increased by supplying, for example, air as the fluid from the hydraulic pump 20 to the stretching air bag 40. With this configuration, opening times of the first and second actuators 2, 3 can be shortened.

A tube through which air is supplied from the hydraulic pump 20 to the opening air bag 30 and the stretching air bag 40 may be shared. With this configuration, a size and manufacturing cost of the soft gripper 1A can be reduced.

The operation of the soft gripper 1A having the above configuration will be described below.

Figure 11A:
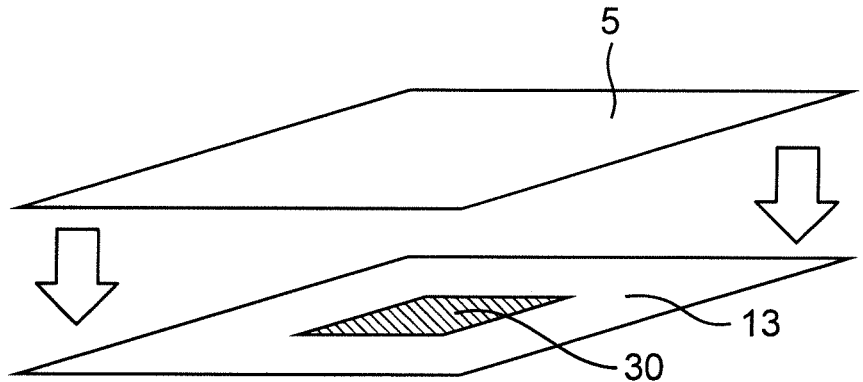
FIG. 11A is a schematic diagram illustrating details of operation of an opening air bag 30 in FIG. 10.
Figure 11B:
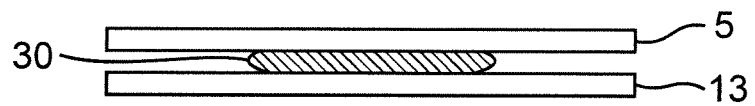
FIG. 11B is a schematic diagram illustrating the details of the operation of the opening air bag 30 in FIG. 10.
Figure 11C:
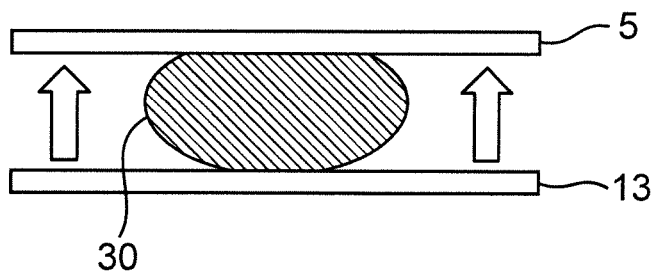
FIG. 11C is a schematic diagram illustrating the details of the operation of the opening air bag 30 in FIG. 10.

FIG. 11 is a schematic diagram illustrating details of the operation of the opening air bag 30 in FIG. 10. FIG. 11A is a schematic diagram illustrating a state immediately before the Hook-and-Loop fastener 5 and the Hook-and-Loop fastener 13 are fixed, FIG. 11B is a schematic diagram illustrating a state in which the Hook-and-Loop fastener 5 and the Hook-and-Loop fastener 13 are fixed, and FIG. 11C is a schematic diagram illustrating a moment when the air is supplied to the opening air bag 30 to release the fixing between the Hook-and-Loop fastener 5 and the Hook-and-Loop fastener 13.

Figure 12:
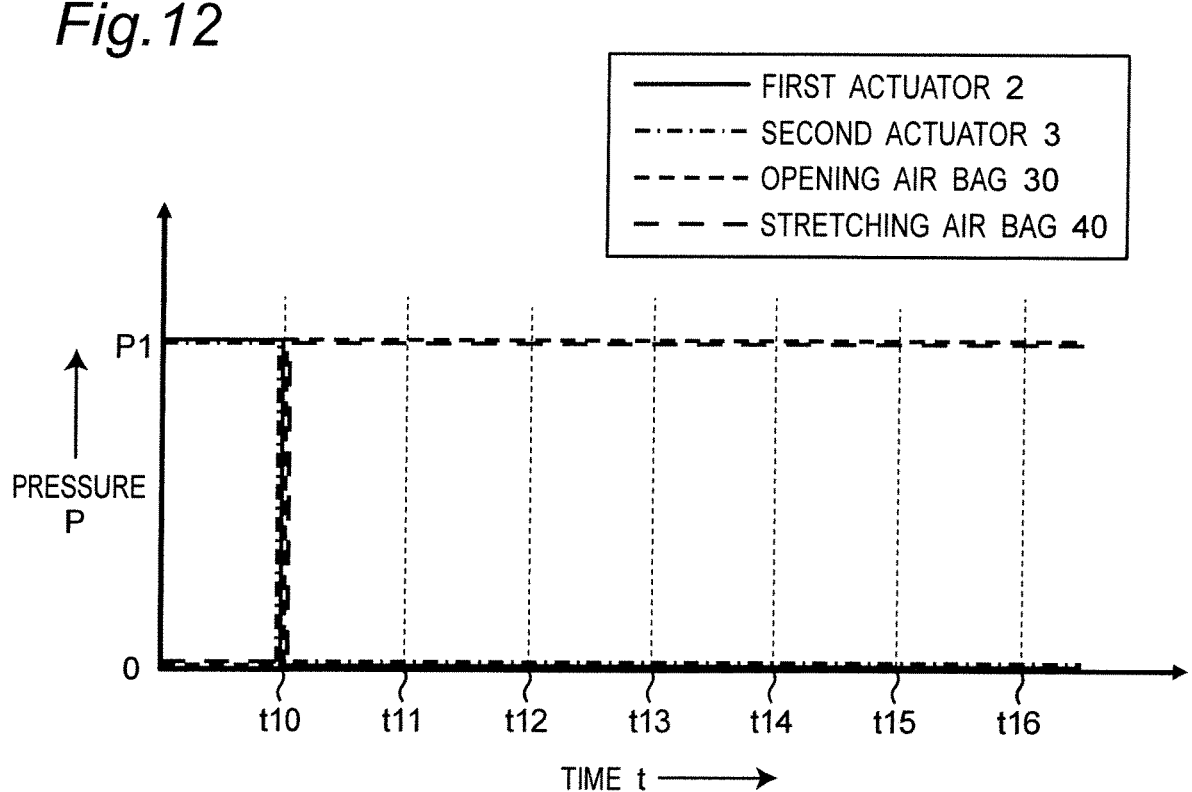
FIG. 12 is a time axis waveform chart illustrating the change in pressure P to time t, the pressure P being applied to the first actuator 2 and the second actuator 3 in FIG. 10.

FIG. 12 is a time axis waveform chart illustrating the change in pressure P to time t, the pressure P being applied to the first and second actuator 2, 3 in FIG. 10, and FIGS. 13A to 13G are schematic diagrams illustrating operating states of the first and the second actuators 2, 3 at each time t in FIG. 12.

Figure 13A:
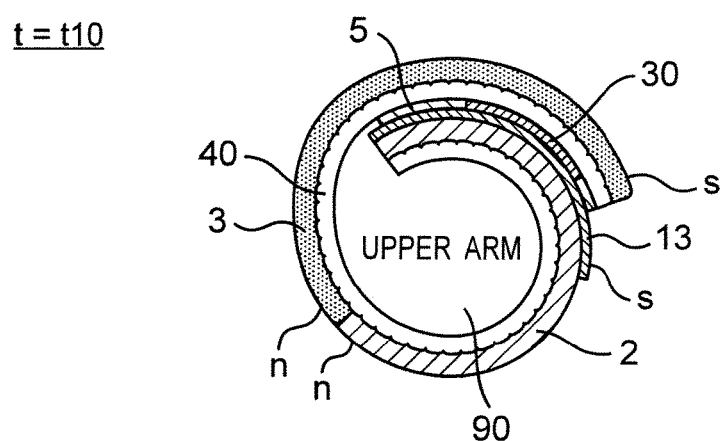
FIG. 13A is a schematic diagram illustrating the operating states of the first actuator 2 and the second actuator 3 at time t10 in FIG. 12.
Figure 13B:
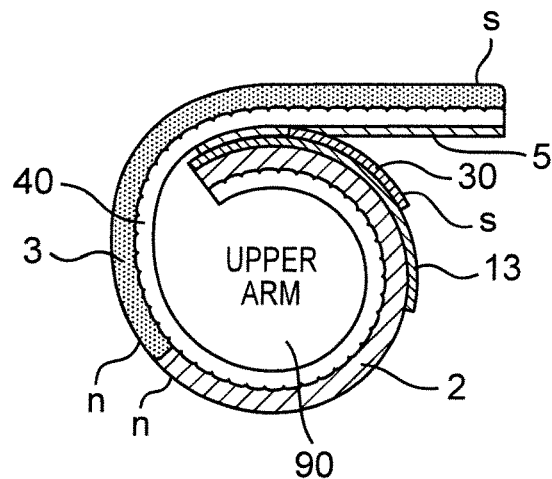
FIG. 13B is a schematic diagram illustrating the operating states of the first actuator 2 and the second actuator 3 at time t11 in FIG. 12.
Figure 13C:
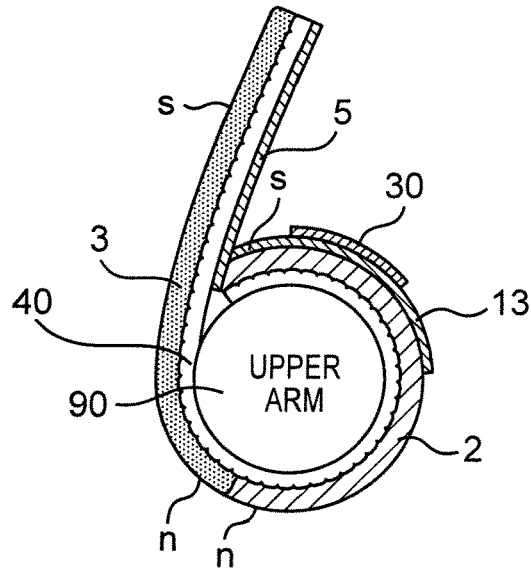
FIG. 13C is a schematic diagram illustrating the operating states of the first actuator 2 and the second actuator 3 at time t12 in FIG. 12.
Figure 13D:
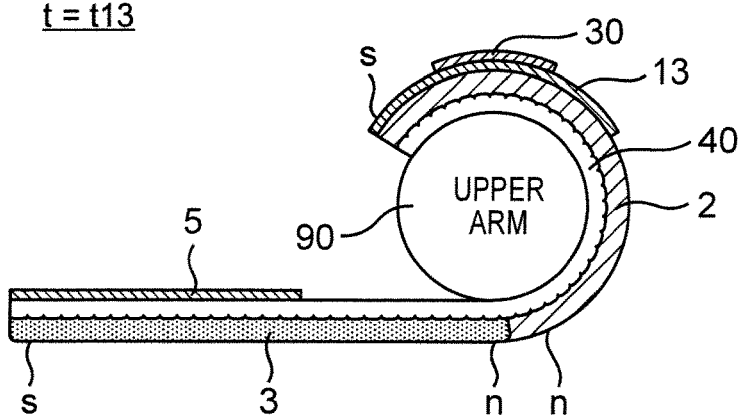
FIG. 13D is a schematic diagram illustrating the operating states of the first actuator 2 and the second actuator 3 at time t13 in FIG. 12.

In FIGS. 12 and 13A, opening operation of the first and second actuators 2, 3 is started at time t10. At this point, both the pressures applied to the first and second actuators 2, 3 are set to zero, and the pressure P1 is applied to the opening air bag 30 and the stretching air bag 40. By continuing this state, the leading end side of the second actuator 3 starts to be released from the outer peripheral surface of the upper arm 90 at time t11 as illustrated in FIG. 13B, and the base side of the second actuator 3 is released from the outer peripheral surface of the upper arm 90 at time t12 subsequent to the leading end side as illustrated in FIG. 13C. As illustrated in FIG. 13D, the second actuator 3 is completely opened at time t13.

Figure 13E:
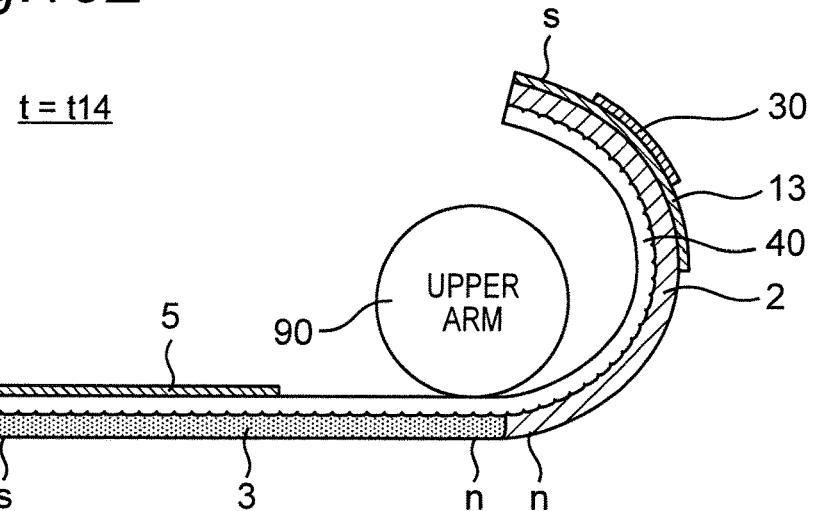
FIG. 13E is a schematic diagram illustrating the operating states of the first actuator 2 and the second actuator 3 at time t14 in FIG. 12.
Figure 13F:
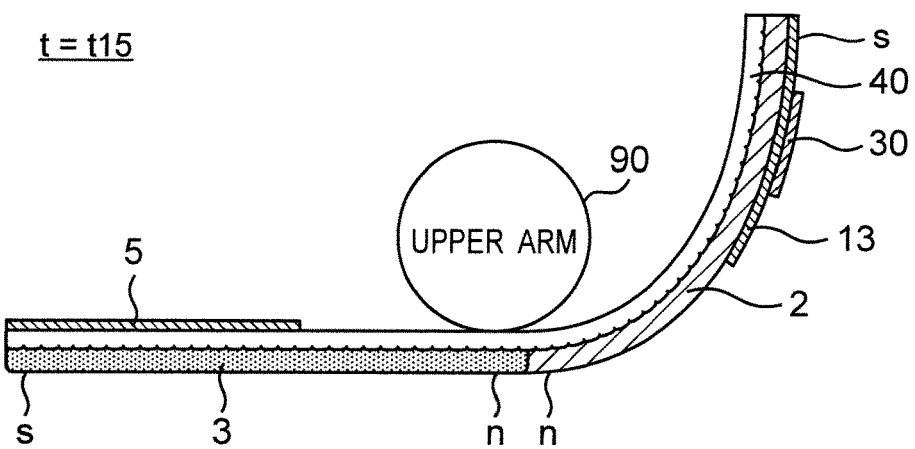
FIG. 13F is a schematic diagram illustrating the operating states of the first actuator 2 and the second actuator 3 at time t15 in FIG. 12.
Figure 13G:
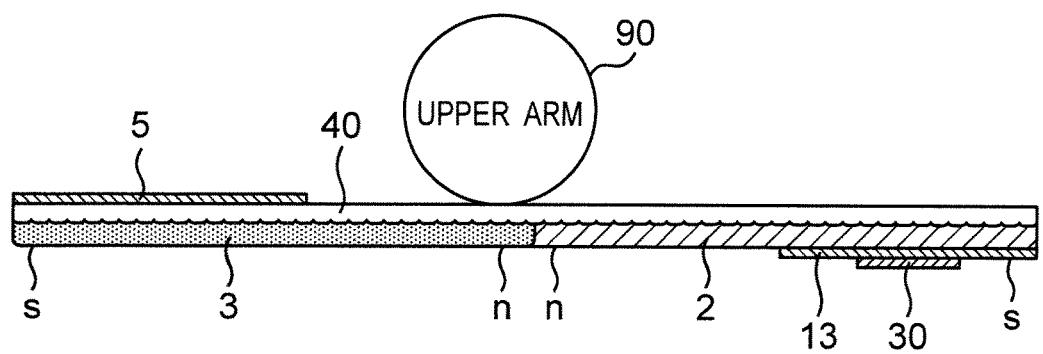
FIG. 13G is a schematic diagram illustrating the operating states of the first actuator 2 and the second actuator 3 at time t16 in FIG. 12.

As illustrated in FIG. 13E, at the time t14, at the same time as the leading end side of the first actuator 2 is released from the outer peripheral surface of the upper arm 90, the base side of the first actuator 2 is released from the outer peripheral surface of the upper arm 90 subsequent to the leading end side. This state is further continued as illustrated in FIG. 13F, and the first and second actuators 2, 3 are completely opened at time t16 as illustrated in FIG. 13G. At this point, since the air is supplied to not only the opening air bag 30 but also the stretching air bag 40, the speed at which the first actuator 2 is released from the outer peripheral surface of the upper arm 90 is enhanced. In the second embodiment, the air is simultaneously supplied from the hydraulic pump 20 to the opening air bag 30 and the stretching air bag 40. With this configuration, the opening speed is further enhanced, so that the first and second actuators 2, 3 can be opened in a short time. The air may sequentially be supplied to the opening air bag 30 and the stretching air bag 40.

Third Embodiment

Figure 14:
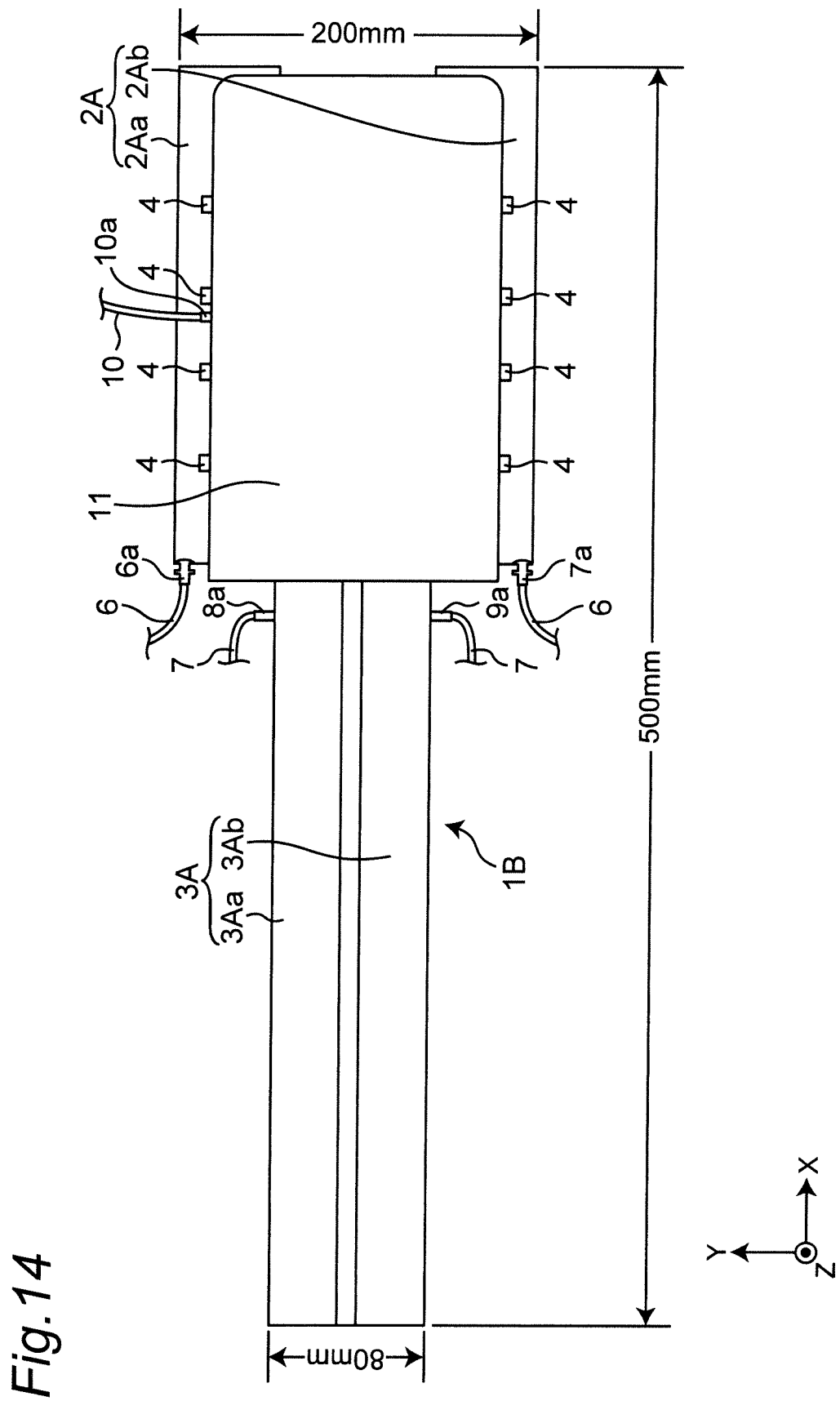
FIG. 14 is a top view illustrating an appearance of a blood pressure measuring cuff according to a third embodiment of the present invention.

FIG. 14 is a top view illustrating an appearance of a blood pressure measuring cuff according to the third embodiment of the present invention, and FIG. 15 is an exploded perspective view illustrating a structure of the blood pressure measuring cuff in FIG. 14. The blood pressure measuring cuff in FIG. 14 includes the measurement air bag 11 used to measure the blood pressure and a soft gripper 1B. As illustrated in FIG. 15, the soft gripper 1B is different from the soft gripper 1 illustrated in FIG. 2 in that the base plastic film 12 and the Hook-and-Loop fasteners 5, 13 are eliminated, that a first actuator 2A is provided instead of the first actuator 2, and that a second actuator 3A is provided instead of the second actuator 3.

As illustrated in FIG. 15, compared with the first actuator 2 in FIG. 2, the first actuator 2A includes first bending type actuator units 2Aa, 2Ab instead of the first bending type actuator units 2a, 2b and second bending type actuator units 3Aa, 3Ab instead of the second bending type actuator units 3a, 3b. The first bending type actuator units 2Aa, 2Ab and the second bending type actuator units 3Aa, 3Ab are constructed with the fluid bag 15A in which the fluid can be stored. The fluid bag 15A has a bag structure including a first sheet member 15Aa, and a second sheet member 15Ab. Since the second sheet members 15Ab is subjected to the folding process called the pleat, when the air pressure is applied to the bag structure, a difference in surface area occurs to generate the bending motion. Details of the fluid bag 15A will be described below with reference to FIGS. 16A and 16B. Assuming that the length direction of each of the actuators 2A, 3A is the X-axis direction, that the width direction is the Y-axis direction, and that the thickness direction is the Z-axis direction, the soft gripper 1B has the length of approximately 500 mm in the X-axis direction, the first actuator 2A has the width of approximately 200 mm in the Y-axis direction, and the second actuator 3A has the width of approximately 80 mm in the Y-axis direction.

The first and second actuators 2A, 3A extend from the bases n toward opposite sides to each other. When receiving the supply of the fluid, each of the first and second actuators 2A, 3A sequentially surrounds the object from the side of the base n toward the side of the leading end s of the each of the first and second actuators 2A, 3A. When the soft gripper 1B is detached from the object, the fluid is exhausted from the first and second actuators 2A, 3A to which the fluid was supplied. Consequently, the bending states of the first and second actuators 2A, 3A, which are bent to surround the object, are eliminated and removed from the object.

In the third embodiment, with respect to the width direction perpendicular to the longitudinal direction in which the first and second actuators 2A, 3A extend, one of the sides of the leading ends s of the first and second actuators 2A, 3A is divided in two portions, and the other side of the leading end s of the first and second actuators 2A, 3A is disposed between the two divided portions. With this configuration, the soft gripper can wind around the object without a gap when surrounding the object.

The air supply ports 6a, 7a, 8a, 9a are provided in the fluid bags 15A of the first bending type actuator units 2Aa, 2Ab and the second bending type actuator units 3Aa, 3Ab, respectively, such that the fluid can be supplied to and discharged from each of the fluid bags 15A. In the first embodiment, gas such as air is used as the fluid. However, the fluid is not limited to the air, but liquid such as water may be used. The fluid is supplied from the hydraulic pump (see FIG. 5) that is of the fluid supply source to the fluid bags 15A connected to the air supply ports 6a, 7a, 8a, 9a through the tubes 6, 7. For example, after the fluid is simultaneously supplied to the first bending type actuator units 2Aa, 2Ab from the outside such as the hydraulic pump through the air supply ports 6a, 7a to pressurize the first actuator 2A, the fluid is simultaneously supplied to the second bending type actuator units 3Aa, 3Ab through the air supply ports 8a, 9a to pressurize the second actuator 3A. Consequently, it is possible to control the timing at which the leading end s of the first actuator 2A is bent along the outer peripheral surface of the object and the timing at which the leading end s of the second actuator 3A is bent along the outer peripheral surface of the object. For example, the first actuator 2A is sequentially bent from the side of the base n to the side of the leading end s, and then the second actuator 3A is sequentially bent from the side of the base n toward the side of the leading end s.

Figure 16A:
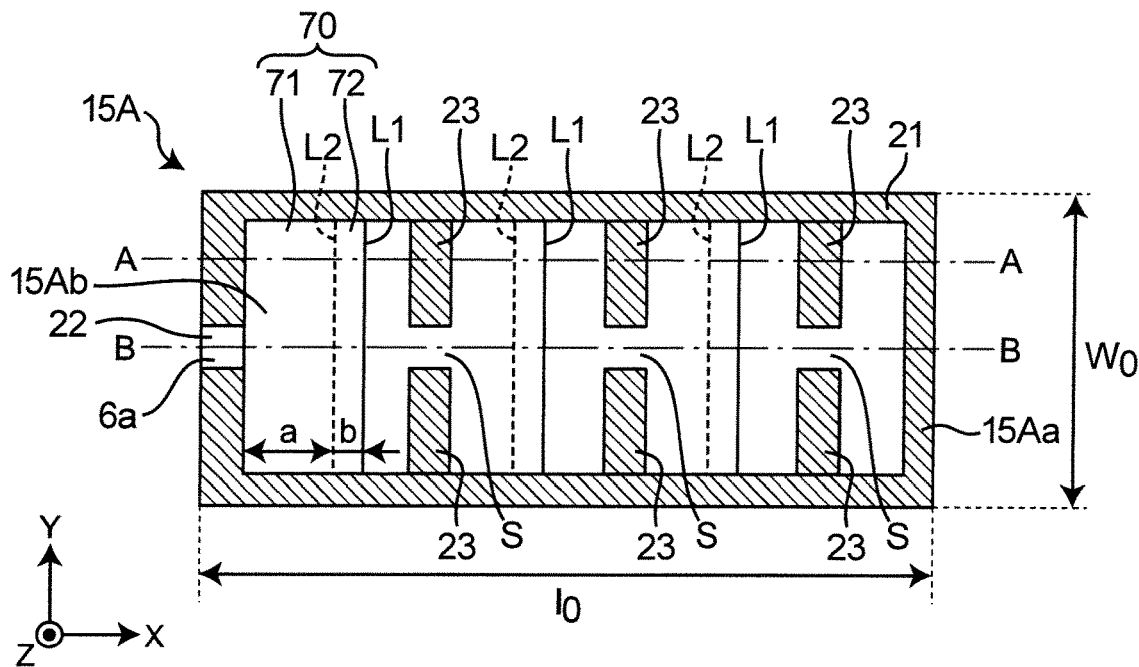
FIG. 16A is a schematic plan view illustrating a fluid bag 15A in FIG. 15.
Figure 16B:
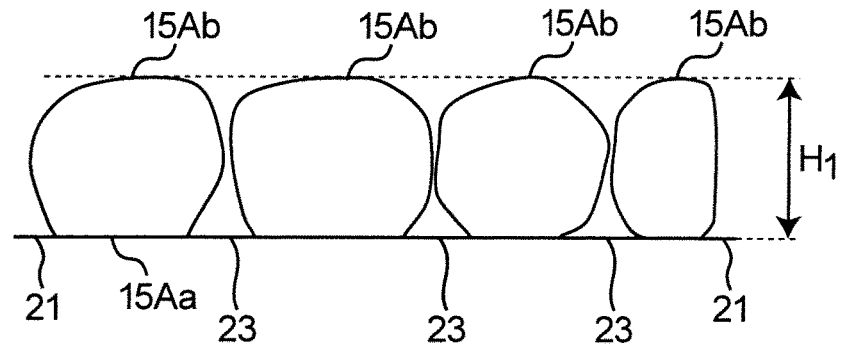
FIG. 16B is a longitudinal sectional view taken along line A-A in FIG. 16A.
Figure 16C:
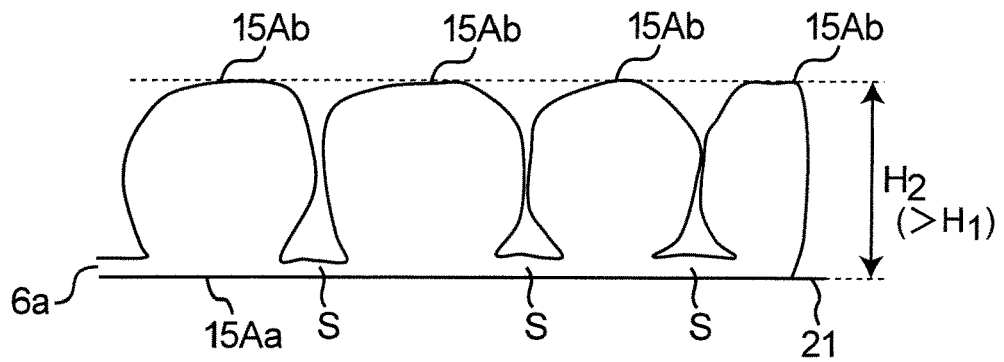
FIG. 16C is a longitudinal sectional view taken along line B-B in FIG. 16A.

FIG. 16A is a schematic plan view illustrating the fluid bag 15A in FIG. 15. FIG. 16B is a longitudinal sectional view taken along line A-A in FIG. 16A, and FIG. 16C is a longitudinal sectional view taken along line B-B in FIG. 16A.

As illustrated in FIG. 16A, each of the first sheet member 15Aa and the second sheet member 15Ab is constructed with the sheet member having the substantially rectangular shape in the XY planar view, the dimension in the length direction (X-axis direction) of the second sheet member 15Ab is longer than the dimension $I_0$ in the length direction of the first sheet member 15Aa, and the dimension W1 in the width direction (Y-axis direction) of the second sheet member 15Ab is longer than the dimension W0 in the width direction of the first sheet member 15Aa. At this point, it is assumed that the length directions of the first sheet member 15Aa and the second sheet member 15Ab are the X-axis direction, that the width directions of the first sheet member 15Aa and the second sheet member 15Ab are the Y-axis direction, and that the thickness directions of the first sheet member 15Aa and the second sheet member 15Ab are the Z-axis direction.

As illustrated in FIG. 16A, the second sheet member 15Ab is divided in the length direction to form the plurality of expandable pleats 70, and each of the pleat 70 includes the outside pleat 71 located outside and the inside pleat 72 folded inside. The outside pleat 71 and the inside pleat 72 are formed by being folded back at a pleat folding line L1 constituting a mountain of the pleat 70 and a pleat folding line L2 constituting a valley. The pleat folding line L1 and the pleat folding line L2 are provided such that a dimension a in the length direction of the outside pleat 71 is longer than a dimension b in the length direction of the inside pleat 72 when the pleat 70 is formed.

When the bag structure is formed using the first sheet member 15Aa and the second sheet member 15Ab having different surface areas, in order to form the space (fluid chamber) in which the fluid is stored, the first sheet member 15Aa and the second sheet member 15Ab are thermally welded while the corner of the second sheet member 15Ab is aligned with the corner (welded portion) 21 of the first sheet member 15Aa indicated by hatching in FIG. 16A. At this point, a portion where the dimension a in the length direction of the outside pleat 71 of the second sheet member 15b and the dimension b in the length direction of the inside pleat 72 overlap with each other is also thermally welded, the overlapping portion being aligned with the welded portion 21 of the first sheet member 15a. Consequently, the fluid can be prevented from leaking out of the fluid chamber to the outside.

The first sheet member 15Aa and the second sheet member 15Ab are thermally welded while a part of the second sheet member 15Ab is aligned with the welded portion 23 of the first sheet member 15Aa indicated by hatching in FIG. 16A. Consequently, as illustrated in FIGS. 16B and 16C, a throttle S that is of a first throttle is provided in the fluid bag 15A at one or a plurality of points in the longitudinal direction of the fluid bag 15A. Each of the fluid bags receives the supply of the fluid from the outside through the first or second air supply port. The fluid is supplied from the side of the base toward the side of the leading end through the first throttles provided at one or a plurality of points in the length direction. Consequently, each of the fluid bags is sequentially bent from the base or the specific point toward the side of the leading end in the length direction. It is preferable that the fluid bags are separately pressurized. This enables a time difference of bending to be provided such that the fluid bag 15A is sequentially bent from the base n toward the side of the leading end s with respect to the longitudinal direction of the fluid bag 15A. With this configuration, the sides of the bases n of the first and second actuators 2A, 3A are bent along the outer peripheral surface of the object, and then the sides of the leading ends s are bent along the outer peripheral surface of the object. Thus, the same pressure is preferably applied to each of the first and second actuators 2A, 3A without pressurizing the first and second actuators 2A, 3A in the longitudinal direction a plurality of times. Consequently, the pressurization control is easily performed when the first and second actuators 2A, 3A are bent.

As illustrated in FIGS. 16B and 16C, the fluid bag 15A includes a large-swelling portion and a small-swelling portion along the longitudinal direction. That is, a swelling H2 in FIG. 16C is larger than a swelling H1 in FIG. 16B. Thus, bending force is large in the large-swelling portion, and bending force is small in the small-swelling portion. With this configuration, the large-swelling portion having the large bending force moves similarly to a joint of a human finger, and the small-swelling portion having the small bending force moves similarly to the finger other than the joint. Thus, it is possible to grip the object like a human hand as a whole. In FIG. 16A, the non-welded portion 22 in which the first sheet member 15Aa and the second sheet member 15Ab are not thermally welded is provided in order to provide the air supply port 6a.

The operation of the soft gripper 1B having the above configuration will be described below.

The operation of the soft gripper 1B when the pressures applied to the first and second actuators 2A, 3A using the hydraulic pump 20 in FIG. 5 are set to 15 kPa will be described below.

FIGS. 17A to 17I are schematic diagrams illustrating operating states of the first and second actuators 2A, 3A.

Figure 17A:
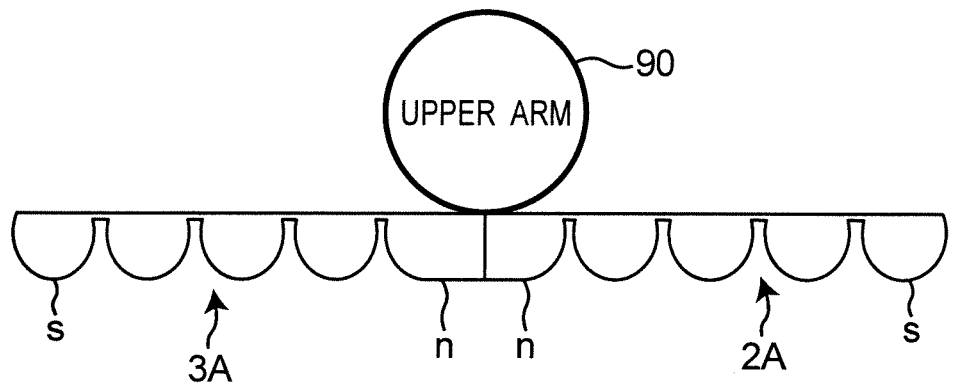
FIG. 17A is a schematic diagram illustrating first operating states of a first actuator 2A and a second actuator 3A in FIG. 14.

First, as illustrated in FIG. 17A, the pressures applied to the first and second actuators 2A, 3A are set to zero (non-pressurized). At this point, the upper arm 90 is placed on the surface of the measurement airbag 11 of the soft gripper 1B (identical to FIG. 6A).

Figure 17B:
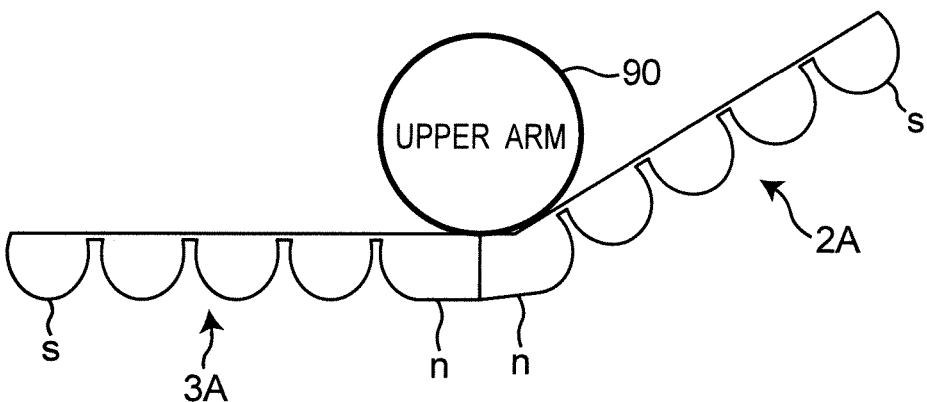
FIG. 17B is a schematic diagram illustrating second operating states of the first actuator 2A and the second actuator 3A in FIG. 14.

Then, a pressure P1 is applied only to the first actuator 2A (the second actuator 3A remains in the non-pressurized state). At this point, as illustrated in FIG. 17B, the side of the base n of the first actuator 2A starts to be bent along the outer peripheral surface of the upper arm 90.

Figure 17C:
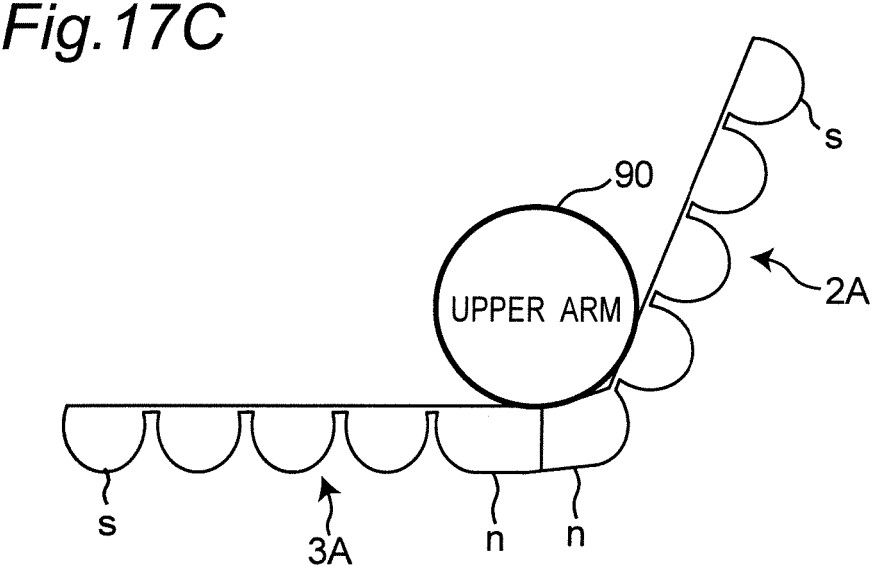
FIG. 17C is a schematic diagram illustrating third operating states of the first actuator 2A and the second actuator 3A in FIG. 14.

When the state in which the pressure P1 is applied only to the first actuator 2A is continued (the second actuator 3A remains in the non-pressurized state), the side of the base n of the first actuator 2A is bent along the outer peripheral surface of the upper arm 90 as illustrated in FIG. 17C.

Figure 17D:
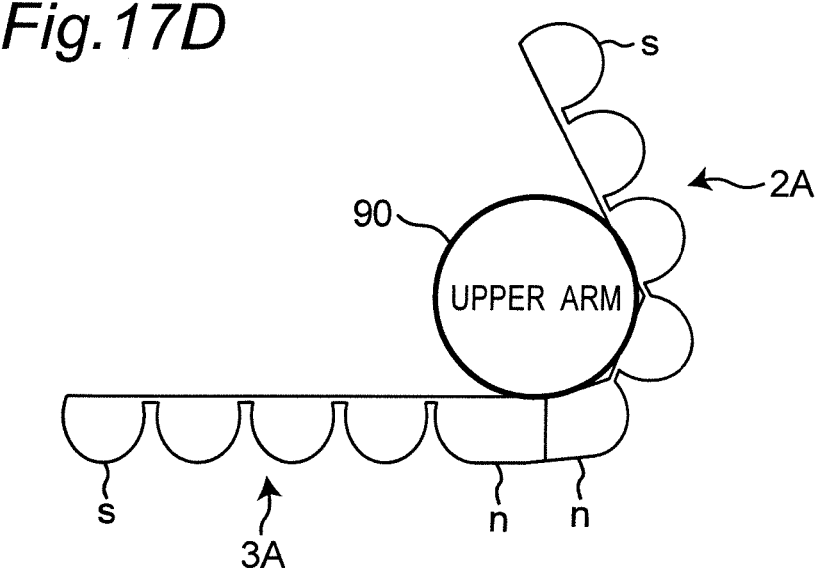
FIG. 17D is a schematic diagram illustrating fourth operating states of the first actuator 2A and the second actuator 3A in FIG. 14.

When the state in which the pressure P1 is applied only to the first actuator 2A is further continued (the second actuator 3A remains in the non-pressurized state), a central portion of the first actuator 2A is bent along the outer peripheral surface of the upper arm 90 as illustrated in FIG. 17D.

Figure 17E:
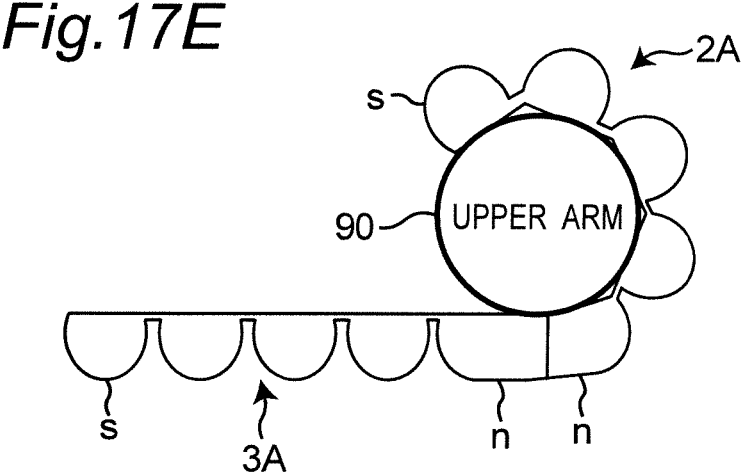
FIG. 17E is a schematic view illustrating fifth operating states of the first actuator 2A and the second actuator 3A in FIG. 14.

When the state in which the pressure P1 is applied only to the first actuator 2A is further continued, the leading end side of the first actuator 2A is further bent along the outer peripheral surface of the upper arm 90 to wrap the upper arm 90 as illustrated in FIG. 17E (identical to FIG. 6B).

Figure 17F:
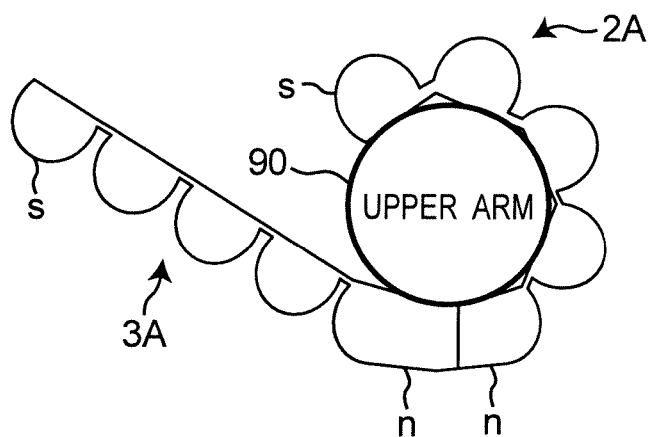
FIG. 17F is a schematic diagram illustrating sixth operating states of the first actuator 2A and the second actuator 3A in FIG. 14.

Then, the pressure P1 is also applied to the second actuator 3A while the pressure P1 is applied to the first actuator 2A. At this point, as illustrated in FIG. 17F, the side of the base n of the second actuator 3A starts to be bent along the outer peripheral surface of the upper arm 90.

Figure 17G:
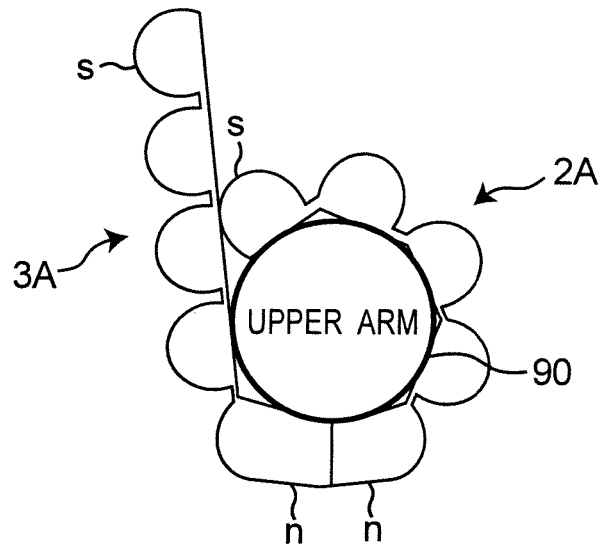
FIG. 17G is a schematic diagram illustrating seventh operating states of the first actuator 2A and the second actuator 3A in FIG. 14.

When the state in which the pressure P1 is applied to the first and second actuators 2A, 3A is further continued, the side of the base n of the second actuator 3A is bent along the outer peripheral surface of the upper arm 90 as illustrated in FIG. 17G.

Figure 17H:
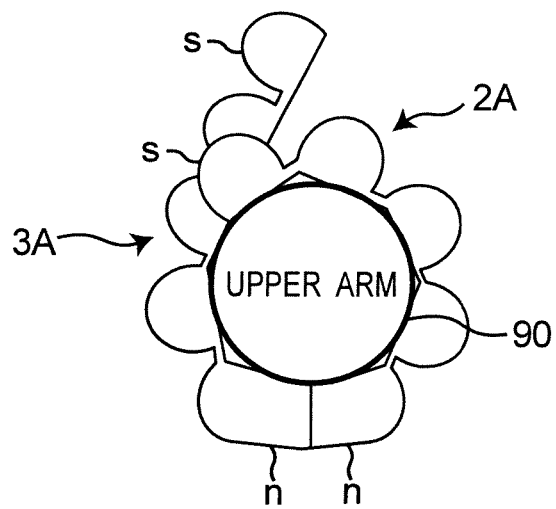
FIG. 17H is a schematic diagram illustrating eighth operating states of the first actuator 2A and the second actuator 3A in FIG. 14.
Figure 17I:
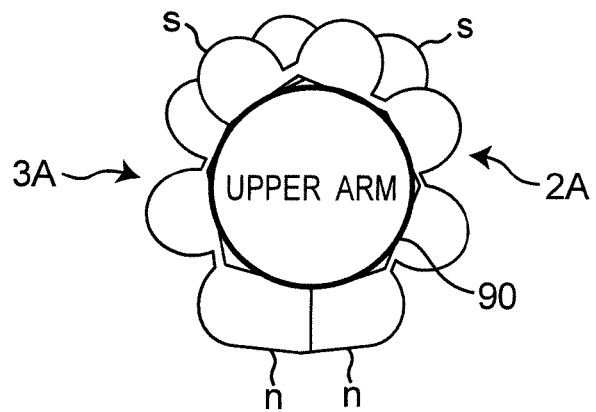
FIG. 17I is a schematic diagram illustrating ninth operating states of the first actuator 2A and the second actuator 3A in FIG. 14.

When the state in which the pressure P1 is applied to the first and second actuators 2A, 3A is further continued, the central portion of the second actuator 3A is bent along the outer peripheral surface of the upper arm 90 subsequent to the base side as illustrated in FIG. 17H. When the state is continued, the leading end side of the second actuator 3A is further bent along the outer peripheral surface of the upper arm 90 to wrap the upper arm 90 as illustrated in FIG. 17I (identical to FIG. 6C).

Fourth Embodiment

Figure 18:
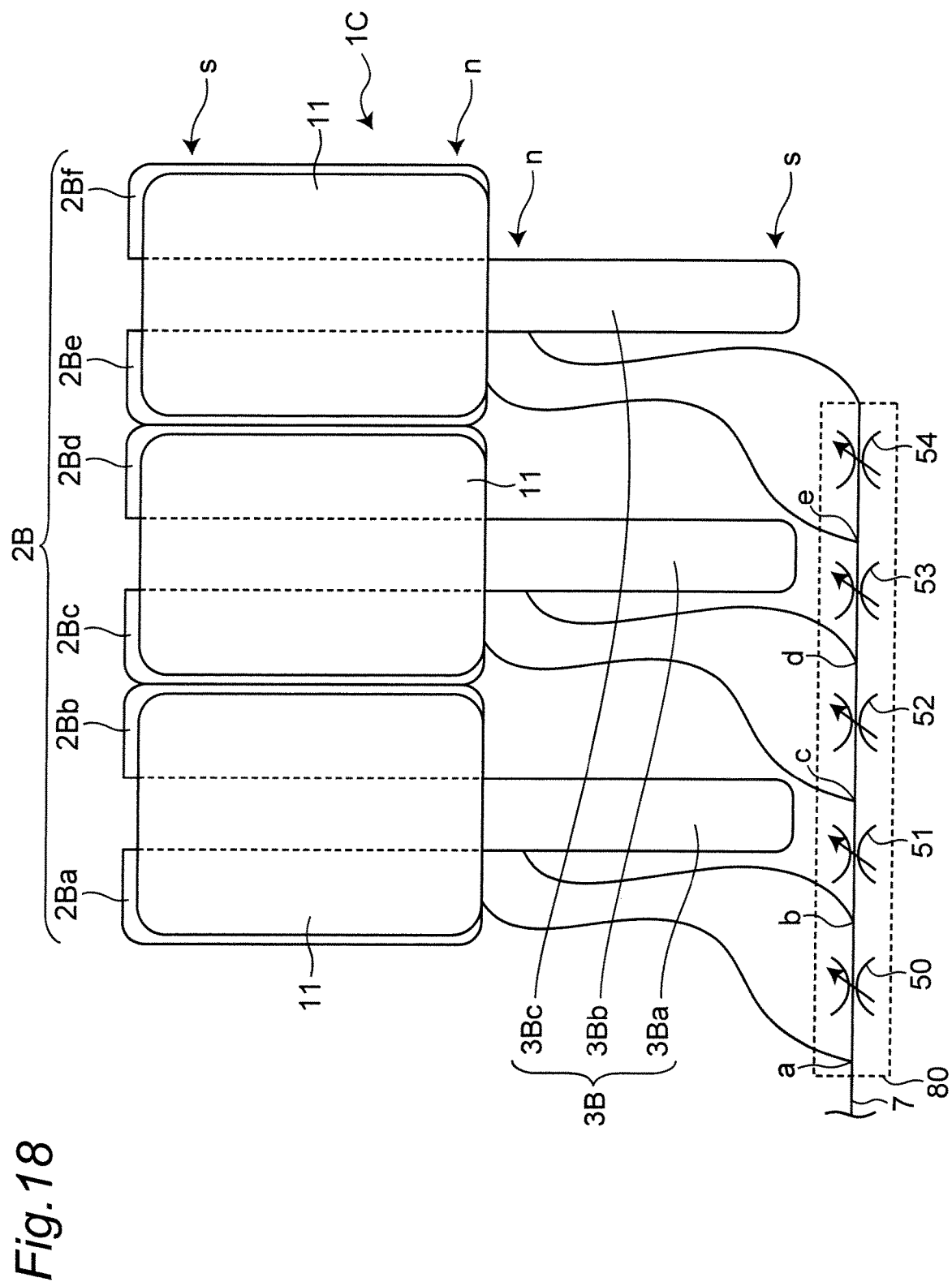
FIG. 18 is a top view illustrating an appearance of a soft gripper 1C according to a fourth embodiment of the present invention.

FIG. 18 is a top view illustrating an appearance of a soft gripper 1C according to a fourth embodiment of the present invention. In the soft gripper 1B of the third embodiment, with respect to the width direction perpendicular to the longitudinal direction in which the first and second actuators 2A, 3A extend, the sides of the leading ends s of the first and second actuators 2A, 3A are divided into two portions, and the second bending type actuator units 3Aa, 3Ab constituting the second actuator 3A are disposed between the two divided portions. On the other hand, in the soft gripper 1C of FIG. 18, the side of the leading end s of a first actuator 2B is divided into four portions, and second bending type actuator units 3Ba, 3Bb, 3Bc constituting a second actuator 3B are disposed among the four divided portions. At this point, the side of the leading end s of the first actuator 2B is constructed with first bending type actuator units 2Ba, 2Bb, 2Bc, 2Bd, 2Be, 2Bf, the first bending type actuator units 2Bb, 2Bc being disposed adjacent to each other, and also the first bending type actuator 2Bd, 2Be being disposed adjacent to each other.

The operation of the soft gripper 1C having the above configuration will be described below. The operation of the soft gripper 1C when the pressures applied to the first and second actuators 2B, 3B using the hydraulic pump 20 in FIG. 5 are set to 15 kPa will be described below.

In the fourth embodiment, as illustrated in FIG. 18, in a tube 7, a pressurization unit 80 that pressurizes the first and second actuators 2B, 3B in order from one side in an elongated direction of the object is provided at a preceding stage of the first and second actuators 2B, 3B of the soft gripper 1C. The pressurization unit 80 includes one flow path through which the fluid is supplied from the outside to its one end (the left end in FIG. 18) and throttles 50 to 54 interposed in the portions, which are connected to the first and second actuators 2B, 3B, in the flow path.

The pressurization unit 80 includes a branch point a that supplies the fluid from the pressure source to the first bending type actuator units 2Ba, 2Bb, a branch point b that supplies the fluid from the pressure source to the second bending type actuator unit 3Ba, a branch point c that supplies the fluid from the pressure source to the first bending type actuator units 2Bc, 2Bd, a branch point d that supplies the fluid from the pressure source to the second bending type actuator unit 3Bb, and a branch point e that supplies the fluid from the pressure source to the first bending type actuator units 2Be, 2Bf.

The pressurization unit 80 includes the throttle 50 interposed between the branch point a and the branch point b, the throttle 51 interposed between the branch point b and the branch point c, the throttle 52 interposed between the branch point c and the branch point d, the throttle 53 interposed between the branch point d and the branch point e, and the throttle 54 interposed between the branch point e and the second bending type actuator unit 3Bc.

The fluid is supplied from the hydraulic pump (see FIG. 5), which is of the supply source of the fluid, to each fluid bag through the tube 7. A procedure for bending each bending type actuator unit will be described in detail below.

First, the fluid is simultaneously supplied from the hydraulic pump to the first bending type actuator units 2Ba, 2Bb through the branch point a. Consequently, the leading ends s of the first bending type actuator units 2Ba, 2Bb are bent along the outer peripheral surface of the object.

Then, the fluid passing the throttle 50 is supplied to the second bending type actuator unit 3Ba through the branch point b. Consequently, the second bending type actuator unit 3Ba is bent along the object while being delayed from the first bending type actuator units 2Ba, 2Bb simultaneously bent along the object.

Then, the fluid passing the throttle 51 is simultaneously supplied to the first bending type actuator units 2Bc, 2Bd through the branch point c. Consequently, the first bending type actuator units 2Bc, 2Bd are simultaneously bent along the object while being delayed from the second bending type actuator unit 3Ba bent along the object.

Then, the fluid passing the throttle 52 is supplied to the second bending type actuator unit 3Bb through the branch point d. Consequently, the second bending type actuator unit 3Bb is bent along the object while being delayed from the first bending type actuator units 2Bc, 2Bd bent along the object.

Then, the fluid passing the throttle 53 is simultaneously supplied to the first bending type actuator units 2Be, 2Bf through the branch point e. Consequently, the first bending type actuator units 2Be, 2Bf are simultaneously bent along the object while being delayed from the second bending type actuator unit 3Bb bent along the object.

Then, the fluid passing the throttle 54 is supplied to the second bending type actuator unit 3Bc. Consequently, the second bending type actuator unit 3Bc is bent along the object while being delayed from the first bending type actuator units 2Be, 2Bf bent along the object, the bending type actuators that are of all the fluid bags surround the object, and the operation is ended. This enables the control of the timing at which the leading end s of each fluid bag is bent along the outer peripheral surface of the object. Therefore, the timing of supplying the fluid from the hydraulic pump to each fluid bag can be changed by the simple configuration in which the throttle is interposed in one flow path, such as the tube 7, which passes the fluid.

Fifth Embodiment

Figure 19:
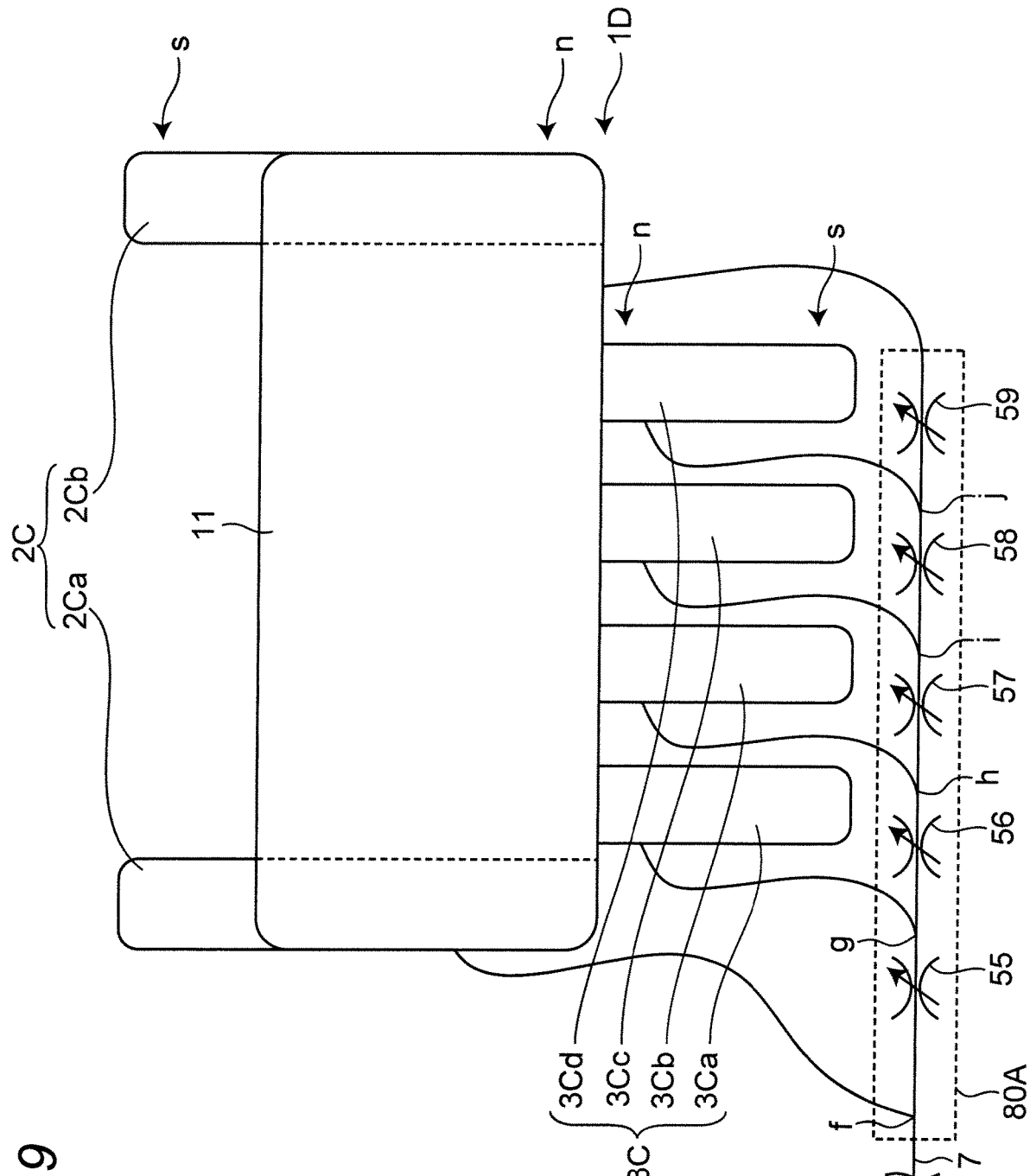
FIG. 19 is a top view illustrating an appearance of a soft gripper 1D according to a fifth embodiment of the present invention.

FIG. 19 is a top view illustrating an appearance of a soft gripper 1D according to a fifth embodiment of the present invention. In the soft gripper 1B of the third embodiment, with respect to the width direction perpendicular to the longitudinal direction in which the first and second actuators 2A, 3A extend, the sides of the leading ends s of the first actuator 2A are divided in two portions, and the second bending type actuator units 3Aa, 3Ab constituting the second actuator 3A are disposed between the two divided portions. On the other hand, in the soft gripper 1D of FIG. 19, the side of the leading end s of a first actuator 2C is divided into two portions, and four of second bending type actuator units 3Ca, 3Cb, 3Cc, 3Cd constituting a second actuator 3C are disposed between the two divided portions.

The operation of the soft gripper 1D having the above configuration will be described below. The operation of the soft gripper 1D when the pressures applied to the first and second actuators 2C, 3C using the hydraulic pump 20 in FIG. 5 are set to 15 kPa will be described below.

In the fifth embodiment, as illustrated in FIG. 19, in the tube 7, a pressurization unit 80A that pressurizes the first and second actuators 2C, 3C in order from one side in the elongated direction of the object is provided at the preceding stage of the first and second actuators 2C, 3C of the soft gripper 1D. The pressurization unit 80A includes one flow path through which the fluid is supplied from the outside to its one end (the left end in FIG. 19) and throttles 55 to 59 interposed in the portions, which are connected to the first and second actuators 2C, 3C, in the flow path.

The pressurization unit 80A includes a branch point f that supplies the fluid from the pressure source to the first bending type actuator unit 2Ca, a branch point g that supplies the fluid from the pressure source to the second bending type actuator unit 3Ca, a branch point h that supplies the fluid from the pressure source to the second bending type actuator unit 3Cb, a branch point i that supplies the fluid from the pressure source to the second bending type actuator unit 3Cc, and a branch point j that supplies the fluid from the pressure source to the second bending type actuator unit 3Cd.

The pressurization unit 80A includes the throttle 55 interposed between the branch point f and the branch point g, the throttle 56 interposed between the branch point g and the branch point h, the throttle 57 interposed between the branch point h and the branch point i, the throttle 58 interposed between the branch point i and the branch point j, and the throttle 59 interposed between the branch point j and the first bending type actuator unit 2Cb.

The fluid is supplied from the hydraulic pump (see FIG. 5), which is of the supply source of the fluid, to each fluid bag through the tube 7. A procedure for bending each bending type actuator unit will be described in detail below.

First, the fluid is supplied from the hydraulic pump to the first bending type actuator unit 2Ca through the branch point f. Consequently, the leading end s of the first bending type actuator unit 2Ca is bent along the outer peripheral surface of the object.

Then, the fluid passing the throttle 55 is supplied to the second bending type actuator unit 3Ca through the branch point g. Consequently, the second bending type actuator unit 3Ca is bent along the object while being delayed from the first bending type actuator unit 2Ca bent along the object.

Then, the fluid passing the throttle 56 is supplied to the second bending type actuator unit 3Cb through the branch point h. Consequently, the second bending type actuator unit 3Cb is bent along the object while being delayed from the second bending type actuator unit 3Ca bent along the object.

Then, the fluid passing the throttle 57 is supplied to the second bending type actuator unit 3Cc through the branch point i. Consequently, the second bending type actuator unit 3Cc is bent along the object while being delayed from the second bending type actuator unit 3Cb bent along the object.

Then, the fluid passing the throttle 58 is supplied to the second bending type actuator unit 3Cd through the branch point j. Consequently, the second bending type actuator unit 3Cd is bent along the object while being delayed from the second bending type actuator unit 3Cc bent along the object.

Then, the fluid passing the throttle 59 is supplied to the first bending type actuator unit 2Cb. Consequently, the first bending type actuator unit 2Cb is bent along the object while being delayed from the second bending type actuator unit 3Cd bent along the object, all the fluid bags surround the object, and the operation is ended. This enables the control of the timing at which the leading end s of each fluid bag is bent along the outer peripheral surface of the object. Therefore, the timing of supplying the fluid from the hydraulic pump to each fluid bag can be changed by the simple configuration in which the throttle is interposed in one flow path, such as the tube 7, which passes the fluid.

Sixth Embodiment

Figure 20:
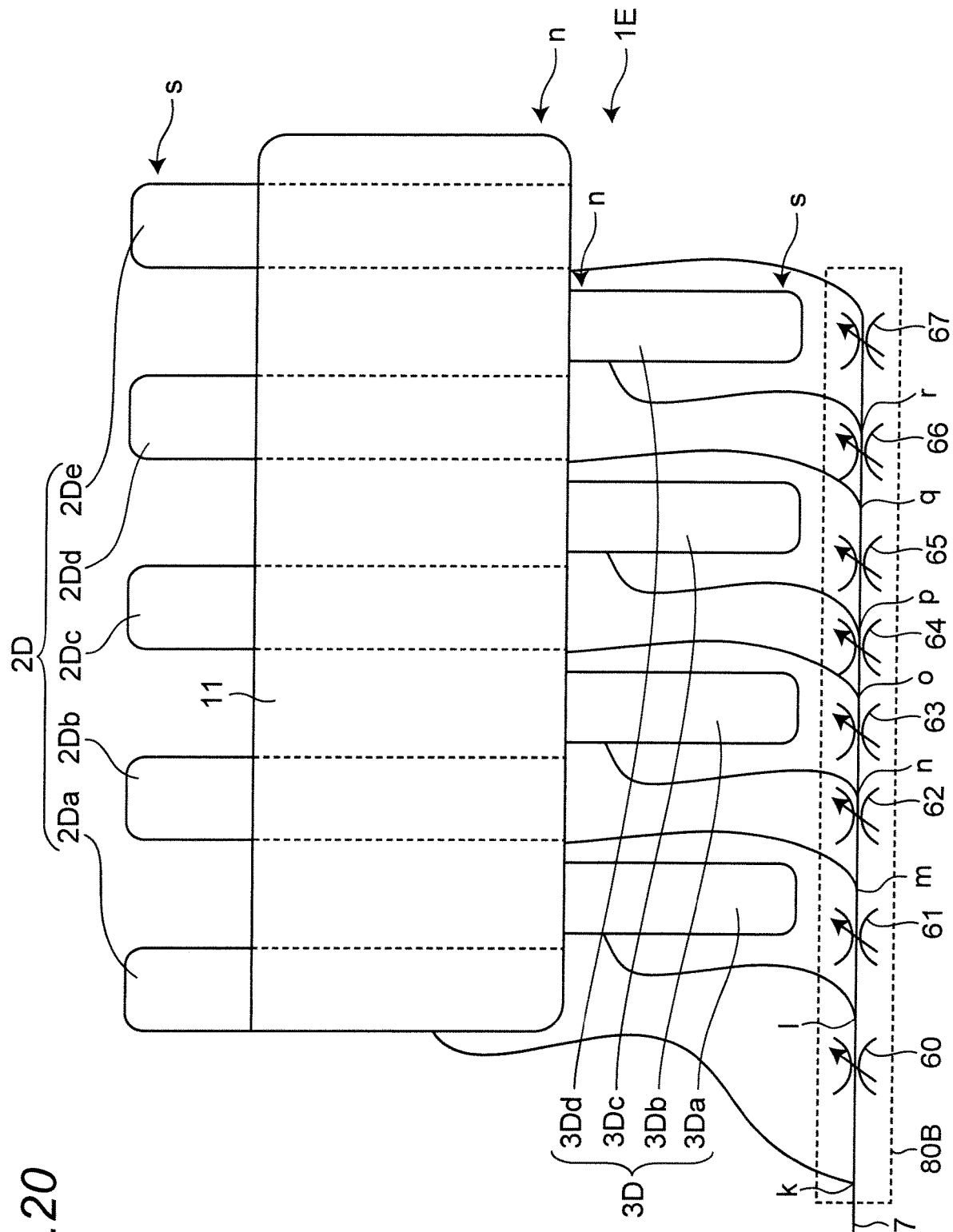
FIG. 20 is a top view illustrating an appearance of a soft gripper 1E according to a sixth embodiment of the present invention.

FIG. 20 is a top view illustrating an appearance of a soft gripper 1E according to a sixth embodiment of the present invention. In the soft gripper 1B of the third embodiment, with respect to the width direction perpendicular to the longitudinal direction in which the first and second actuators 2A, 3A extend, the sides of the leading ends s of the first and second actuators 2A, 3A are divided in two portions, and the second bending type actuator units 3Aa, 3Ab constituting the second actuator 3A are disposed between the two divided portions. On the other hand, in the soft gripper 1E of FIG. 20, the side of the leading end s of a first actuator 2D is divided into five portions of second bending type actuator units 2Da, 2Db, 2Dc, 2Dd, 2De, and four of second bending type actuator units 3Da, 3Db, 3Dc and 3Dd constituting a second actuator 3D are disposed among the divided five portions.

The operation of the soft gripper 1E having the above configuration will be described below. The operation of the soft gripper 1E when the pressures applied to the first and second actuators 2D, 3D using the hydraulic pump 20 in FIG. 5 are set to 15 kPa will be described below.

In the sixth embodiment, as illustrated in FIG. 20, in the tube 7, a pressurization unit 80B that pressurizes the first and second actuators 2D, 3D in order from one side in the elongated direction of the object is provided at the preceding stage of the first and second actuators 2D, 3D of the soft gripper 1E. The pressurization unit 80B includes one flow path through which the fluid is supplied from the outside to its one end (the left end in FIG. 20) and throttles 60 to 67 interposed in the portions, which are connected to the first and second actuators 2D, 3D, in the flow path.

The pressurization unit 80B includes a branch point k that supplies the fluid from the pressure source to the first bending type actuator unit 2Da, a branch point 1 that supplies the fluid from the pressure source to the second bending type actuator unit 3Da, a branch point m that supplies the fluid from the pressure source to the first bending type actuator unit 2Db, a branch point n that supplies the fluid from the pressure source to the second bending type actuator unit 3Db, a branch point o that supplies the fluid from the pressure source to the first bending type actuator unit 2Dc, a branch point p that supplies the fluid from the pressure source to the second bending type actuator unit 3Dc, a branch point q that supplies the fluid from the pressure source to the first bending type actuator unit 2Dd, and a branch point r that supplies the fluid from the pressure source to the second bending type actuator unit 3Dd.

The pressurization unit 80B includes the throttle 60 interposed between the branch point k and the branch point 1, the throttle 61 interposed between the branch point 1 and the branch point m, the throttle 62 interposed between the branch point m and the branch point n, the throttle 63 inserted between the branch point n and the branch point o, the throttle 64 interposed between the branch point o and the branch point p, the throttle 65 interposed between the branch point p and the branch point q, the throttle 66 interposed between the branch point q and the branch point r, and the throttle 67 interposed between the branch point r and the first bending type actuator unit 2De.

The fluid is supplied from the hydraulic pump (see FIG. 5), which is of the supply source of the fluid, to each fluid bag through the tube 7. A procedure for bending each bending type actuator unit will be described in detail below.

Figure 21:
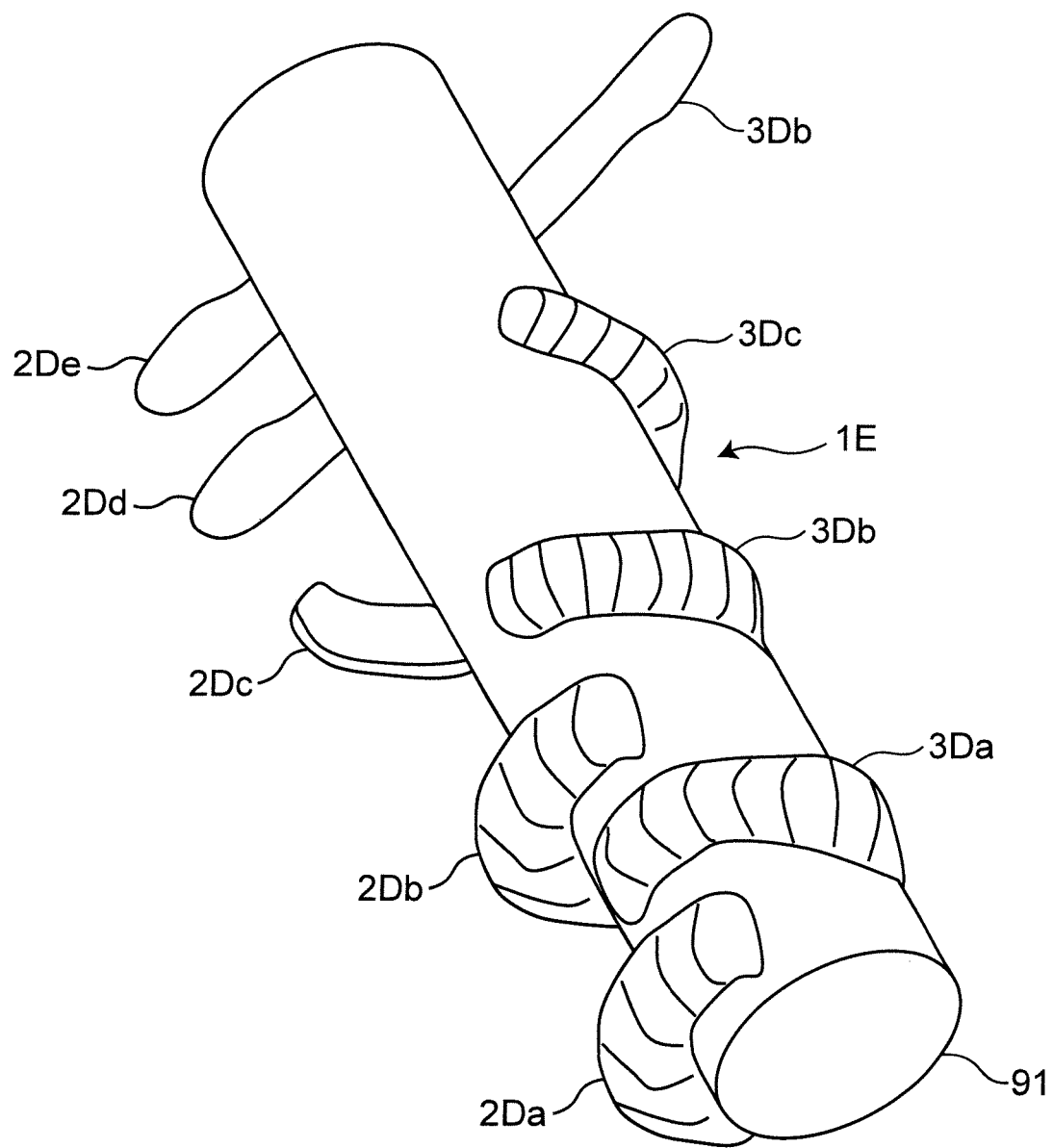
FIG. 21 is a schematic diagram illustrating the operation of the soft gripper 1E in FIG. 20.

FIG. 21 is a schematic diagram illustrating the operation of the soft gripper 1E in FIG. 20. FIG. 21 illustrates the operation in which the soft gripper 1E wraps an object 91 long in one direction.

First, the fluid is supplied from the hydraulic pump to the first bending type actuator unit 2Da through the branch point k. Consequently, the leading end s of the first bending type actuator unit 2Da is bent along the outer peripheral surface of the object 91.

Then, the fluid passing the throttle 60 is supplied to the second bending type actuator unit 3Da through the branch point 1. Consequently, the second bending type actuator unit 3Da is bent along the object 91 while being delayed from the first bending type actuator unit 2Da bent along the object 91.

Then, the fluid passing the throttle 61 is supplied to the first bending type actuator unit 2Db through the branch point m. Consequently, the first bending type actuator unit 2Db is bent along the object 91 while being delayed from the second bending type actuator unit 3Da bent along the object 91.

Then, the fluid passing the throttle 62 is supplied to the second bending type actuator unit 3Db through the branch point n. Consequently, the second bending type actuator unit 3Db is bent along the object 91 while being delayed from the first bending type actuator unit 2Db bent along the object 91.

Then, the fluid passing the throttle 63 is supplied to the first bending type actuator unit 2Dc through the branch point o. Consequently, the first bending type actuator unit 2Dc is bent along the object 91 while being delayed from the second bending type actuator unit 3Db bent along the object 91.

Then, the fluid passing the throttle 64 is supplied to the second bending type actuator unit 3Dc through the branch point p. Consequently, the second bending type actuator unit 3Dc is bent along the object 91 while being delayed from the first bending type actuator unit 2Dc bent along the object 91.

Then, the fluid passing the throttle 65 is supplied to the first bending type actuator unit 2Dd through the branch point q. Consequently, the first bending type actuator unit 2Dd is bent along the object 91 while being delayed from the second bending type actuator unit 3Dc bent along the object 91.

Then, the fluid passing the throttle 66 is supplied to the second bending type actuator unit 3Dd through the branch point r. Consequently, the second bending type actuator unit 3Dd is bent along the object 91 while being delayed from the first bending type actuator unit 2Dd bent along the object 91.

Then, the fluid passing the throttle 67 is supplied to the first bending type actuator unit 2De. Consequently, the first bending type actuator unit 2De is bent along the object 91 while being delayed from the second bending type actuator unit 3Dd bent along the object 91, all the fluid bags surround the object 91, and the operation is ended. This enables the control of the timing at which the leading end s of the fluid bag is bent along the outer peripheral surface of the object 91. Therefore, the timing of supplying the fluid from the hydraulic pump to each fluid bag can be changed by the simple configuration in which the throttle is interposed in one flow path, such as the tube 7, which passes the fluid.

The third to sixth embodiments do not include the configurations of the flexible plate 14 of the first and second embodiments. However, the third to sixth embodiments may further include the configuration of the flexible plate 14 that changes the bending rigidity of the fluid bag. In this case, the bending speed along the object is further enhanced.

The configurations of the Hook-and-Loop fasteners 5, 13, the opening air bag 30, and the stretching air bag 40 in the first and second embodiments may also be incorporated in the third to sixth embodiments.

Seventh Embodiment

Figure 22:
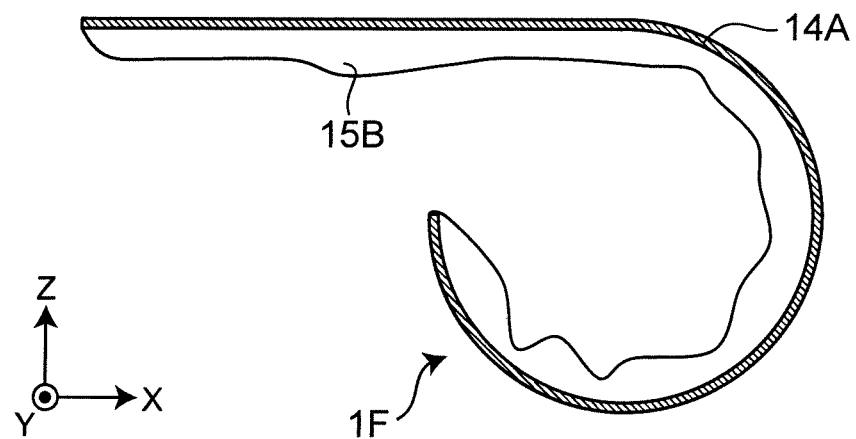
FIG. 22 is a side view illustrating an appearance of a soft gripper 1F according to a seventh embodiment of the present invention.

FIG. 22 is a side view illustrating an appearance of a soft gripper 1F according to the seventh embodiment of the present invention. The soft gripper 1F in FIG. 22 includes a flexible plate 14A having an elongated shape and a bending type actuator unit 15B that is stuck to the flexible plate 14A so as to overlap the flexible plate 14A.

The flexible plate 14A in FIG. 22 has the configuration similar to the flexible plate 14 of the first and second embodiments. The bending type actuator unit 15B in FIG. 22 has a bag structure similar to that of the bending type actuator unit of the third to sixth embodiments.

In a natural state before the soft gripper 1F is wound around the object, the soft gripper 1F has a shape in which the soft gripper 1F is bent onto the opposite side to the direction in which the object is surrounded. With this configuration, an apparent dimension (length) in the X direction of the soft gripper 1F can be shortened. Since the size of the soft gripper 1F can be further miniaturized, a volume for storage can further be reduced. Therefore, the storage is facilitated.

Additionally, the soft gripper 1F sequentially surrounds the object while releasing the bending. With this configuration, the object can be surrounded even for the narrow space around the soft gripper 1F.

The operation of the soft gripper 1F having the above configuration will be described below.

FIGS. 23A-23F are schematic diagrams illustrating the operation of the soft gripper 1F in FIG. 22. FIGS. 23A-23F illustrate the operation in which the soft gripper 1F wraps around the upper arm 90.

Figure 23A:
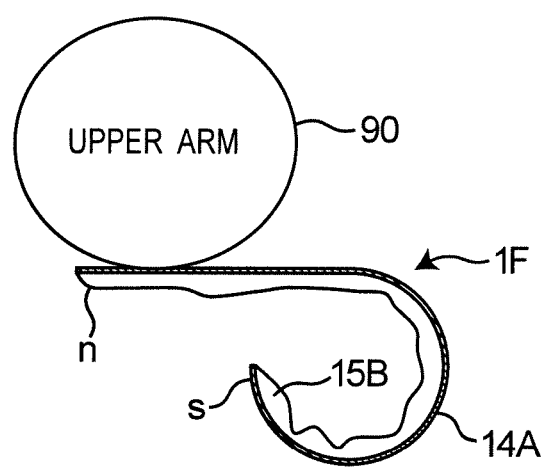
FIG. 23A is a schematic diagram illustrating a first state of the operation of the soft gripper 1F in FIG. 22.
Figure 23B:
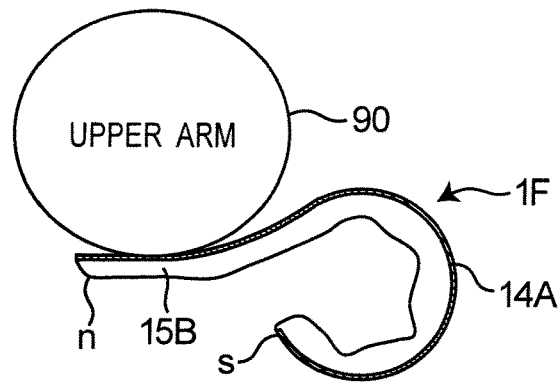
FIG. 23B is a schematic diagram illustrating a second state of the operation of the soft gripper 1F in FIG. 22.

First, as illustrated in FIG. 23A, the upper arm 90 is placed on the base n on the flexible plate 14A of the soft gripper 1F. When the pressure is applied to the soft gripper 1F, the leading end s of the soft gripper 1F bent onto the opposite side to the direction in which the upper arm 90 that is of the object is surrounded moves in the direction in which the bending is released (see FIG. 23B).

Figure 23C:
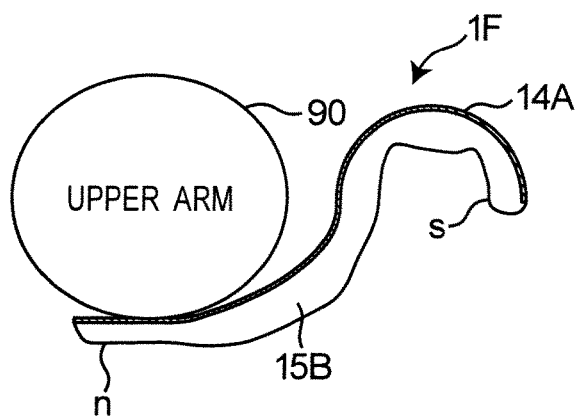
FIG. 23C is a schematic view illustrating a third state of the operation of the soft gripper 1F in FIG. 22.

When pressure is further applied to the soft gripper 1F, the bending of the soft gripper 1F toward the opposite side to the upper arm 90 is further released as illustrated in FIG. 23C.

Figure 23D:
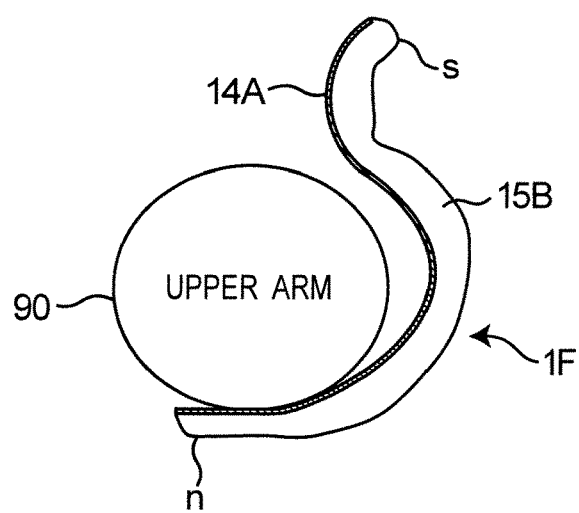
FIG. 23D is a schematic view illustrating a fourth state of the operation of the soft gripper 1F in FIG. 22.

When pressure is further applied to the soft gripper 1F, the bending of the soft gripper 1F toward the opposite side to the upper arm 90 is further released as illustrated in FIG. 23D, and the side of the leading end s of the soft gripper 1F moves toward the side of the upper arm 90.

Figure 23E:
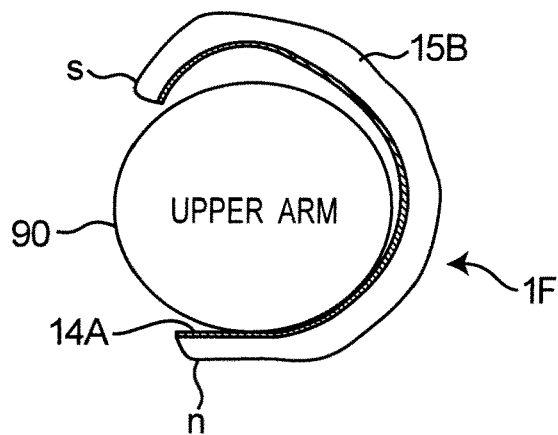
FIG. 23E is a schematic view illustrating a fifth state of the operation of the soft gripper 1F in FIG. 22.

When pressure is further applied to the soft gripper 1F, the side of the leading end s of the soft gripper 1F starts to be bent along the outer peripheral surface as illustrated in FIG. 23E.

Figure 23F:
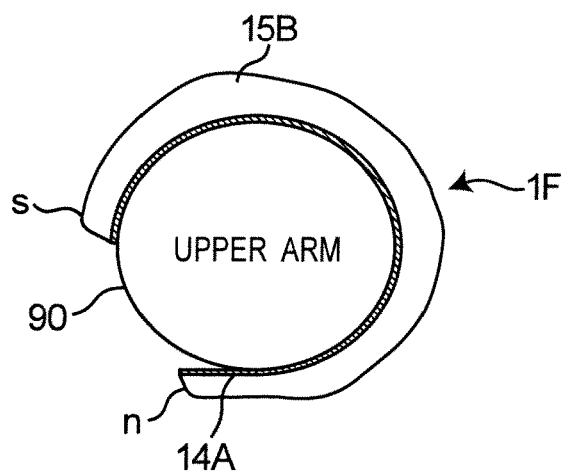
FIG. 23F is a schematic view illustrating a sixth state of the operation of the soft gripper 1F in FIG. 22.

When pressure is further applied to the soft gripper 1F, the side of the leading end s of the soft gripper 1F is further bent along the outer peripheral surface to wrap the upper arm 90 as illustrated in FIG. 23F.

Figure 24A:
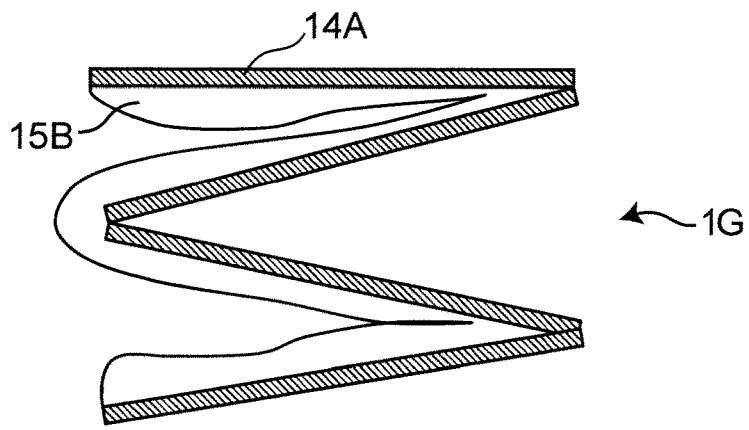
FIG. 24A is a side view illustrating an appearance of a soft gripper 1G according to a first modification of the seventh embodiment of the present invention.
Figure 24B:
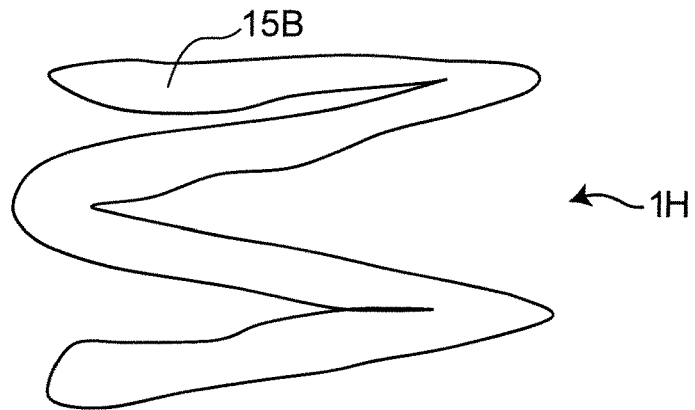
FIG. 24B is a side view illustrating an appearance of a soft gripper 1H according to a second modification of the seventh embodiment of the present invention.

In the seventh embodiment, the soft gripper 1F is configured to be bent only once on the opposite side to the direction in which the object is surrounded. In contrast, as illustrated in FIG. 24A, a soft gripper 1G may be configured to be folded on the opposite side to the direction in which the object is surrounded. In FIG. 24A, the soft gripper 1G has the shape in the natural state before the soft gripper 1G is wound around the object. As illustrated in FIG. 24B, a soft gripper 1H may be constructed only with the bending type actuator unit 15B. In FIG. 24B, the soft gripper 1H has the shape in the natural state before the soft gripper 1H is wound around the object. Even in these cases, the operation similar to that of the seventh embodiment can be obtained, and the apparent dimension (length) in the X direction of the soft grippers 1G, 1H can further be shortened. Since the size of the soft grippers 1G, 1H can be further reduced, the volume for storage can further be reduced. Therefore, the storage is further facilitated.

In the seventh embodiment and its modifications, the configuration of the Hook-and-Loop fasteners 5, 13 of the first embodiment may be incorporated in the end of the soft gripper, or the configurations of the opening air bag 30 and the stretching air bag 40 of the second embodiment may be incorporated.

As described above, in the embodiments, the soft grippers 1 to 1K that surround and grip the outer peripheral surface of the upper arm 90, the object 91, or the sphere 92, the soft grippers 1 to 1K include the elongated first actuators 2 to 2F and the elongated second actuators 3 to 3F, which are deformed in response to the supply of the fluid. The first actuators 2 to 2F and the second actuators 3 to 3F extend from bases n of the first and second actuators 2 to 2F, 3 to 3F toward opposite sides to each other. When receiving the supply of the fluid, the first and second actuators 2 to 2F, 3 to 3F sequentially surround the upper arm 90, the object 91, or the sphere 92 in a manner that each of the first and second actuators 2 to 2F, 3 to 3F sequentially surrounds it from the base n or the specific point C between the base n and the leading end s toward the side of the leading end s.

In the soft grippers 1 to 1K of the present invention, when receiving the supply of the fluid, the first and second actuators 2 to 2F, 3 to 3F sequentially surround the upper arm 90, the object 91, or the sphere 92 from the bases n of the first and second actuators 2 to 2F, 3 to 3F or the specific point C between the base n and the leading end s toward the side of the leading end s.

Thus, in the soft grippers 1 to 1K of this embodiment, the upper arm 90, the object 91, or the sphere 92 can automatically be surrounded and gripped using the first and second actuators 2 to 2F, 3 to 3F.

When the soft grippers 1 to 1K are detached from the upper arm 90, the object 91 or the sphere 92, the fluid is exhausted from the first and second actuators 2 to 2F, 3 to 3F to which the fluid was supplied. Consequently, the bending states of the first and second actuators 2 to 2F, 3 to 3F, which are bent to surround the upper arm 90, the object 91, or the sphere 92, are eliminated, and the first and second actuators 2 to 2F, 3 to 3F are detached from the upper arm 90, the object 91, or the sphere 92.

In the soft grippers 1 to 1K of the embodiment, in the first and second actuators 2 to 2F, 3 to 3F, bending rigidity on the side of the base n is smaller than bending rigidity on the side of the leading end s.

In the soft grippers 1 to 1K of the present invention, when the same pressure is applied to the first and second actuators 2 to 2F, 3 to 3F, the first and second actuators 2 to 2F, 3 to 3F are bent from the side of the base n toward the side of the leading ends to surround the upper arm 90, the object 91, or the sphere 92. In such a case, the pressurization control is easily performed when the first and second actuators 2 to 2F, 3 to 3F are bent. If the bending rigidity of each of the first and second actuators 2 to 2F, 3 to 3F were uniform in the longitudinal direction, the pressurization would be performed at a plurality of levels in the longitudinal direction of the first and second actuators 2 to 2F, 3 to 3F, making the pressurization control complicated and troublesome.

In the soft grippers 1 to 1K of one embodiment, each of the first and second actuators 2 to 2F, 3 to 3F includes the flexible plate 14, 14A, 14B and the fluid bag 15 stuck to the flexible plate 14, 14A, 14B, each of the fluid bags 15 includes a plurality of expandable pleats 70 formed while divided in the length direction, each of the fluid bags 15 includes the first and second air supply ports 6a, 7a, 8a, 9a that supplies the fluid, and each of the fluid bags 15, 15A, 15B is separately pressurized by receiving the supply of the fluid from the outside through the first or second air supply ports 6a, 7a, 8a, 9a.

In the soft grippers 1 to 1K of this embodiment, the first and second air supply ports 6a, 7a, 8a, 9a are separately pressurized, the timing at which the leading end s of the first actuators 2 to 2F are bent along the outer peripheral surface of the upper arm 90, the object 91, or the sphere 92 and the timing at which the leading end s of the second actuators 3 to 3F are bent along the outer peripheral surface of the upper arm 90, the object 91, or the sphere 92 can separately be controlled. For example, the first actuators 2 to 2F are sequentially bent from the side of the base n to the side of the leading end s, and then the second actuators 3 to 3F are sequentially bent from the side of the base n toward the side of the leading end s.

In the soft grippers 1 to 1K of one embodiment, each of the first and second actuators 2 to 2F, 3 to 3F include the fluid bags 15A, 15B, each of the fluid bags 15A and 15B includes a plurality of expandable pleats 70 that are formed while divided in the length direction and the first throttle S that is provided at one or a plurality of points so as to be sequentially bent from the base n or the specific point C toward the side of the leading end s in the length direction, each of the fluid bags 15A, 15B includes first and second air supply ports 6a, 7a, 8a, 9a that receive the supply of the fluid at the base n, and each of the fluid bags 15A, 15B is pressurized by receiving the supply of the fluid from an outside through the first or second air supply port 6a, 7a, 8a, 9a.

In the soft grippers 1 to 1K of this embodiment, each of the fluid bags 15A, 15B receives the supply of the fluid from the outside through the first or second air supply ports 6a, 7a, 8a, 9a. The fluid is supplied from the side of the base n toward the side of the leading end s through the first throttles S provided at one or a plurality of points in the length direction. Consequently, each of the fluid bags 15A, 15B is sequentially bent from the base n or the specific point C toward the side of the leading end s in the length direction. It is preferable that the fluid bags 15A, 15B are separately pressurized. Consequently, it is possible to control the timing at which the leading ends s of the first actuators 2 to 2F are bent along the outer peripheral surface of the upper arm 90, the object 91, or the sphere 92 and the timing at which the leading ends s of the second actuators 3 to 3F is bent along the outer peripheral surface of the upper arm 90, the object 91, or the sphere 92. For example, the first actuators 2 to 2F are sequentially bent from the side of the base n to the side of the leading end s, and then the second actuators 3 to 3F are sequentially bent from the side of the base n toward the side of the leading end s.

In the soft grippers 1 to 1K of one embodiment, each of the fluid bags 15A, 15B includes along the length direction, a first portion of large-swelling and a second portion of swelling smaller than that of the first portion.

In the soft grippers 1 to 1K of this embodiment, the bending force is large in the large-swelling portion and the bending force is small in the small-swelling portion. With this configuration, the large-swelling portion having the large bending force moves similarly to a joint of a human finger, and the small-swelling portion having the small bending force moves similarly to the finger other than the joint. Thus, it is possible to grip the object like a human hand as a whole.

The soft grippers 1 to 1K of one embodiment includes:
the Hook-and-Loop fastener 13 provided on the outer periphery of the leading end s of the first actuator 2; and
the Hook-and-Loop fastener 5 provided on the inner periphery of the leading end s of the second actuator 3.

When the upper arm 90 is surrounded by the first and second actuators 2 to 2F, 3 to 3F, the Hook-and-Loop fastener 13 and the Hook-and-Loop fastener 5 are fixed to each other while overlapping each other.

In the soft grippers 1 to 1K of this embodiment, when the upper arm 90, the object 91, or the sphere 92 is surrounded by the first and second actuators 2 to 2F, 3 to 3F, the Hook-and-Loop fastener 13 and the Hook-and-Loop fastener 5 are fixed to each other while overlapping each other. Thus, the upper arm 90 can firmly be fixed with the soft grippers 1 to 1K by receiving the supply of the fluid from the outside.

In the soft grippers 1 to 1K of one embodiment, the opening air bag 30, which detaches the Hook-and-Loop fasteners 5, 13 from each other by receiving the supply of the fluid from the outside, is disposed at the positions corresponding to the Hook-and-Loop fasteners 5, 13.

In the soft grippers 1 to 1K of this embodiment, the opening air bag 30 receives the supply of the fluid, whereby the fixing between the Hook-and-Loop fastener 13 and the Hook-and-Loop fastener 5 is automatically released. Thus, the fixing between the first and second actuators 2 to 2F, 3 to 3F can automatically be released.

In the soft grippers 1 to 1K of one embodiment, the stretching air bag 40 is provided along each surface side of the first and second actuators 2 to 2F, 3 to 3F which comes into contact with the upper arm 90, the object 91, or the sphere 92, so as to eliminate the bending of the first and second actuators 2 to 2F, 3 to 3F and stretch the first and second actuators 2 to 2F, 3 to 3F when the stretching fluid bag 40 receives the supply of the fluid from the outside.

In the soft grippers 1 to 1K of this embodiment, the speed at which the first and second actuators 2 to 2F, 3 to 3F are stretched can be enhanced when the stretching air bag 40 receives the supply of the fluid from the outside. Thus, opening times of the first and second actuators 2 to 2F, 3 to 3F can be shortened.

In the soft grippers 1 to 1K of the embodiment, with respect to the width direction perpendicular to the longitudinal direction in which the first and second actuators 2 to 2F, 3 to 3F extend, one of the sides of the leading ends s of the first and second actuators 2 to 2F, 3 to 3F is divided in two portions, and the other side of the leading end s of the first and second actuators 2 to 2F, 3 to 3F is disposed between the two divided portions.

In the soft grippers 1 to 1K of this embodiment, with respect to the width direction perpendicular to the longitudinal direction in which the first and second actuators 2 to 2F, 3 to 3F extend, one of the sides of the leading ends s of the first and second actuators 2 to 2F, 3 to 3F is divided in two portions, and the other side of the leading end s of the first and second actuators 2 to 2F, 3 to 3F is disposed between the two divided portions. Thus, when surrounding the upper arm 90, the object 91, or the sphere 92, the soft grippers 1 to 1K wind around the upper arm 90, the object 91, or the sphere 92 without a gap.

In the soft grippers 1 to 1K of one embodiment,
with respect to the width direction perpendicular to the longitudinal direction in which the first and second actuators 2 to 2F, 3 to 3F extend, one of the sides of the leading ends s of the first and second actuators 2 to 2F, 3 to 3F is divided in the plurality of portions, and the other side of the leading end s of the first and second actuators 2 to 2F, 3 to 3F is disposed between the plurality of divided portions.

In the soft grippers 1 to 1K of this embodiment, with respect to the width direction perpendicular to the longitudinal direction in which the first and second actuators 2 to 2F, 3 to 3F extend, one of the sides of the leading ends s of the first and second actuators 2 to 2F, 3 to 3F is divided in two portions, and the other side of the leading end s of the first and second actuators 2 to 2F, 3 to 3F is disposed between the two divided portions. Thus, when surrounding the upper arm 90, the object 91, or the sphere 92, the soft grippers 1 to 1K wind around the upper arm 90, the object 91, or the sphere 92 without a gap.

In the soft grippers 1 to 1K of one embodiment, the object 91 has an elongated shape in one direction. The soft grippers 1 to 1K further include the pressurization unit 80 to 80B that sequentially pressurizes the first and second actuators 2 to 2F, 3 to 3F from one side to the other side in an elongated direction of the object 91.

In the soft grippers 1 to 1K of this embodiment, the object 91 having the elongated shape can sequentially be wound around from one side to the other side in the elongated direction of the object 91.

In the soft grippers 1 to 1K of one embodiment, the pressurization units 80 to 80B include one flow path that receives the supply of the fluid from the outside to its one end and the second throttle 50 to 67 interposed between a portion connected to the first actuators 2 to 2F in the flow path and a portion connected to the second actuators 3 to 3F in the flow path.

In the soft grippers 1 to 1K of this embodiment, the timing of supplying the fluid from the hydraulic pump 20 to each of the fluid bags 15 to 15B can be changed by the simple configuration in which the throttle (second throttles 50 to 67) is interposed in one flow path, such as the tube 7, which passes the fluid. Thus, the timings at which the plurality of portions of the divided leading ends s of the first and second actuators 2 to 2F, 3 to 3F are bent along the outer peripheral surface of the object 91 can be controlled.

In the soft grippers 1 to 1K of one embodiment, in a natural state, the first or second actuator 2 to 2F, 3 to 3F has the shape bent or folded on the opposite side to the direction in which the object 91 is surrounded.

In the soft grippers 1 to 1K of this embodiment, the apparent dimension in the longitudinal direction of the soft grippers 1 to 1K can be shortened. Since the size of the soft grippers 1 to 1K can be further miniaturized, a volume for storage can further be reduced. Therefore, the storage is facilitated.

In the soft grippers 1 to 1K of one embodiment, the first or second actuator sequentially surrounds the object 91 while releasing the bending or the folding.

In the soft grippers 1 to 1K of this embodiment, the objects 91 are sequentially surrounded while the bending or the folding is released. With this configuration, the object 91 can be surrounded even for the narrow space around the soft grippers 1 to 1K.

In another aspect, the blood pressure measuring cuff of the present invention includes the soft grippers 1 to 1K.

In the blood pressure measuring cuff of the present invention, when the first and second actuators 2 to 2F, 3 to 3F receive the fluid supply, the soft grippers 1 to 1K provided in the blood pressure measuring cuff successively surrounds the upper arm 90 in a manner that each of the first and second actuators 2 to 2F, 3 to 3F sequentially surrounds it from the base n or the specific point C between the base n and the leading ends toward the side of the leading ends. Thus, it is possible to automatically mount the blood pressure measuring cuff on the upper arm 90 even for elderly persons who have difficulties in tightening or removing the blood pressure measuring cuff by themselves or persons having diseases of the shoulder, so that the elderly persons who have difficulties in tightening or detaching the blood pressure measuring cuff by themselves or the persons having the diseases of the shoulder can measure the blood pressure. Since the arm can automatically be wrapped according to a thickness of the arm corresponding to the person who uses the blood pressure measuring cuff, even a person with a thick arm or thin arm can measure the blood pressure.

In the above embodiments, the object is assumed to be the arm such as the upper arm, but the object is not limited to the arm. The region to be measured may be an upper body, a wrist, or a leg. The object is not limited to the human body region to be measured, but may be an object other than the human body.

Although the present invention is used for the blood pressure measuring cuff, the present invention is not limited to the blood pressure measuring cuff. For example, the present invention can be used for a seatbelt used for vehicles such as a car or an airplane, a rescue robot, an object gripping device that grips soft objects such as a fruit, an amusement plaything such as a crane game machine, an industrial robot used to manufacture a product, a household electric appliance, such as a massage machine, which repeats grasping and releasing operations, and a patient restraint tool that restrains a patient to a bed in a surgical operation or an MRI (Magnetic Resonance Imaging) examination.

As is described above, the soft gripper for fixing a human body of the present disclosure comprises:

an elongated first actuator and an elongated second actuator, which are deformed in response to supply of a fluid;

wherein the first actuator and the second actuator extend from bases of the first and second actuators toward opposite sides to each other, and when receiving the supply of the fluid in a condition that the base or a specific point between the base and a leading end is contact with the object, each of the first and second actuators is deformed along with the outer peripheral surface of the object to surround the object by starting to be bent sequentially from the base or the specific point toward a side of the leading end.

As used herein, the "base" means an end on the side of a connection portion where the first actuator and the second actuator are connected to each other. The "leading end" means an end on the opposite side to the "base".

In the soft gripper of the present disclosure, when receiving the supply of the fluid in a condition that the base or a specific point between the base and a leading end is contact with the object, each of the first and second actuators is deformed along with the outer peripheral surface of the object to surround the object by starting to be bent sequentially from the base or the specific point toward the side of the leading end.

Thus, by the soft gripper of this embodiment, it becomes possible to automatically surround and grip the object while adapting to the thickness of the object using the first and second actuators.

When the soft gripper is detached from the object, the fluid is exhausted from the first and second actuators to which the fluid was supplied. Consequently, the bending states of the first and second actuators, which are bent to surround the object, are eliminated, and the first and second actuators are detached from the object.

In one embodiment of the soft gripper, in each of the first and second actuators, bending rigidity on a side of the base is smaller than bending rigidity on the side of the leading end.

In the soft gripper of this embodiment, when the same pressure is applied to the first and second actuators, the first and second actuators are bent from the side of the base toward the side of the leading end to surround the object. In such a case, pressurization control is easily performed when the first and second actuators are bent. If the bending rigidity of each of the first and second actuators were uniform in the longitudinal direction, the pressurization would be performed at a plurality of levels in the longitudinal direction of the first and second actuators, making the pressurization control complicated and troublesome.

In one embodiment of the soft gripper, each of the first and second actuators includes a flexible plate and a fluid bag stuck to the flexible plate, each of the fluid bags includes a plurality of expandable pleats that are formed while divided in a length direction, each of the fluid bags includes first and second air supply ports that supply the fluid, and each of the fluid bags is separately pressurized by receiving the supply of the fluid from an outside through the first or second air supply port.

As used herein, the "outside" means an outside of the soft gripper.

In the soft gripper of this embodiment, when the first and second air supply ports are separately pressurized, the timing at which the leading end of the first actuator is bent along the outer peripheral surface of the object and the timing at which the leading end of the second actuator is bent along the outer peripheral surface of the object can separately be controlled. For example, the first actuator is sequentially bent from the side of the base toward the side of the leading end, and then the second actuator is sequentially bent from the side of the base toward the side of the leading end.

In one embodiment of the soft gripper, each of the first and second actuators includes a fluid bag, each of the fluid bags includes a plurality of expandable pleats that are formed while divided in a length direction, and a first throttle that is provided at one or a plurality of points so as to be sequentially bent from the base or the specific point toward the side of the leading end in the length direction, each of the fluid bags includes first and second air supply ports that receive the supply of the fluid at the base, and each of the fluid bags is pressurized by receiving the supply of the fluid from an outside through the first or second air supply port.

In the soft gripper of this embodiment, each of the fluid bags receives the supply of the fluid from the outside through the first or second air supply port. The fluid is supplied from the side of the base toward the side of the leading end through the first throttles provided at one or a plurality of points in the length direction. Consequently, each of the fluid bags is sequentially bent from the base or the specific point toward the side of the leading end in the length direction. It is preferable that the fluid bags are separately pressurized. Consequently, it is possible to control timing at which the leading end of the first actuator is bent along an outer peripheral surface of the object, and timing at which the leading end of the second actuator is bent along an outer peripheral surface of the object. For example, the first actuator is sequentially bent from the side of the base toward the side of the leading end, and then the second actuator is sequentially bent from the side of the base toward the side of the leading end.

In one embodiment of the soft gripper, each of the fluid bags includes along the length direction, a first portion of large-swelling and a second portion of swelling smaller than that of the first portion.

In the soft gripper of this embodiment, the bending force is large in the large-swelling portion and the bending force is small in the small-swelling portion. With this configuration, the large-swelling portion having the large bending force moves similarly to a joint of a human finger, and the small-swelling portion having the small bending force moves similarly to the finger other than the joint. Thus, it is possible to grip the object like a human hand as a whole.

One embodiment of the soft gripper comprises:

a first fixing element provided on an outer periphery at the leading end of the first actuator; and a second fixing element provided on an inner periphery at the leading end of the second actuator, wherein the first fixing element and the second fixing element are fixed to each other while overlapping each other when the object is surrounded by the first and second actuators.

In the soft gripper of this embodiment, when the object is surrounded by the first and second actuators, the first fixing element and the second fixing element are fixed to each other while overlapping each other. Thus, the object can firmly be fixed with the soft gripper by receiving the supply of the fluid from the outside.

In one embodiment of the soft gripper, a detaching fluid bag that receives the supply of the fluid from the outside to detach the first and second fixing elements from each other is disposed at positions corresponding to the first and second fixing elements.

In the soft gripper of this embodiment, the fixing between the first fixing element and the second fixing element is automatically released when the detaching fluid bag receives the supply of the fluid. Thus, the fixing between the first and second actuators can automatically be released.

In one embodiment of the soft gripper, a stretching fluid bag is provided along each surface side of the first and second actuators which comes into contact with the object, so as to eliminate the bending of the first and second actuators and stretch the first and second actuators when the stretching fluid bag receives the supply of the fluid from the outside.

In the soft gripper of this embodiment, the speed at which the first and second actuators are stretched can be enhanced when the stretching fluid bag receives the supply of the fluid from the outside. Thus, opening times of the first and second actuators can be shortened.

In one embodiment of the soft gripper, with respect to a width direction perpendicular to a longitudinal direction in which the first and second actuators extend, one of the sides of the leading ends of the first and second actuators is divided into two portions, and the other side of the leading end of the first and second actuators is disposed between the two divided portions.

In the soft gripper of this embodiment, with respect to the width direction perpendicular to the longitudinal direction in which the first and second actuators extend, one of the sides of the leading ends of the first and second actuators is divided in two portions, and the other side of the leading end of the first and second actuators is disposed between the two divided portions. Thus, the soft gripper can wind around the object without a gap when surrounding the object.

In one embodiment of the soft gripper, with respect to a width direction perpendicular to a longitudinal direction in which the first and second actuators extend, one of the sides of the leading ends of the first and second actuators is divided into a plurality of portions, and the other side of the leading end of the first and second actuators is disposed between the plurality of divided portions.

In the soft gripper of this embodiment, with respect to the width direction perpendicular to the longitudinal direction in which the first and second actuators extend, one of the sides of the leading ends of the first and second actuators is divided in two portions, and the other side of the leading end of the first and second actuators is disposed between the two divided portions. Thus, the soft gripper can wind around the object without a gap when surrounding the object.

In one embodiment of the soft gripper, the object has an elongated shape in one direction, the soft gripper further comprising:

a pressurization unit that sequentially pressurizes the first and second actuators from one side to the other side in an elongated direction of the object.

In the soft gripper of this embodiment, the object having an elongated shape can sequentially be wound around from one side to the other side in the elongated direction of the object.

In one embodiment of the soft gripper, the pressurization unit includes one flow path that receives the supply of the fluid from the outside to its one end, and a second throttle interposed between a portion connected to the first actuator in the flow path and a portion connected to the second actuator in the flow path.

In the soft gripper of this embodiment, the timing of supplying the fluid from the hydraulic pump to each fluid bag can be changed by the simple configuration in which the throttle (second throttle) is interposed in one flow path, such as the tube, which passes the fluid. Thus, the timings at which the plurality of portions of the divided leading ends of the first and second actuators are bent along the outer peripheral surface of the object can be controlled.

In one embodiment of the soft gripper, in a natural state, the first or second actuator has a shape bent or folded on an opposite side to a direction in which the object is surrounded.

In the soft gripper of this embodiment, the apparent dimension in the longitudinal direction of the soft gripper can be shortened. Since the size of the soft gripper can be further miniaturized, thus a volume for storage can further be reduced. Therefore, the storage is facilitated.

In one embodiment of the soft gripper, the first or second actuator sequentially surrounds the object while releasing the bending or the folding.

The soft gripper of this embodiment sequentially surrounds the object while releasing the bending or the folding. With this configuration, the object can be surrounded even for the narrow space around the soft gripper.

In another aspect, a blood pressure measuring cuff of the present disclosure comprises the above described soft gripper.

In the blood pressure measuring cuff of the present disclosure, when the first and second actuators receive the supply of the fluid, the soft gripper provided in the blood pressure measuring cuff surrounds the object in a manner that each of the first and second actuators sequentially surrounds it from the base or the specific point between the base and the leading end toward the side of the leading end. Thus, it is possible to automatically mount the blood pressure measuring cuff on the upper arm even for elderly persons who have difficulties in tightening or removing the blood pressure measuring cuff by themselves or persons having diseases of the shoulder, so that they can measure the blood pressure. Since the arm can automatically be wrapped according to a thickness of the arm corresponding to the person who uses the blood pressure measuring cuff, even a person with a thick arm or thin arm can measure the blood pressure.

As is clear from the above description, in the soft gripper and the blood pressure measuring cuff of the present disclosure, the object can automatically be surrounded and gripped.

It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A soft gripper configured to surround and grip an object having a curved outer peripheral surface, the soft gripper comprising:
   an elongated first actuator and an elongated second actuator, which are deformed in response to supply of a fluid;
   wherein the first actuator and the second actuator extend from bases of the first and second actuators toward opposite sides from each other to leading ends of the first and second actuators, respectively, and
   in each of the first actuator and the second actuator, bending rigidity on a side of the base as a whole is smaller than bending rigidity on a side of the leading end as a whole, such that when receiving the supply of the fluid in a condition that the base or a specific point between the base and the leading end is in contact with the object, each of the first and second actuators is deformed along the curved outer peripheral surface of the object to surround the object by starting to be bent sequentially from the base or the specific point toward the side of the leading end.

2. The soft gripper according to claim 1, wherein
   each of the first and second actuators includes a flexible plate and a fluid bag stuck to the flexible plate,
   each of the fluid bags includes a plurality of expandable pleats that are formed while divided in a length direction,
   each of the fluid bags includes first and second air supply ports that supply the fluid, and
   each of the fluid bags is separately pressurized by receiving the supply of the fluid from an outside through the first or second air supply port.

3. The soft gripper according to claim 1, wherein
   each of the first and second actuators includes a fluid bag,
   each of the fluid bags includes a plurality of expandable pleats that are formed while divided in a length direction, and a first throttle that is provided at one or a plurality of points so as to be sequentially bent from the base or the specific point toward the side of the leading end in the length direction,
   each of the fluid bags includes first and second air supply ports that receive the supply of the fluid at the base, and
   each of the fluid bags is pressurized by receiving the supply of the fluid from an outside through the first or second air supply port.

4. The soft gripper according to claim 3, wherein
   each of the fluid bags includes along the length direction, a first portion of large-swelling and a second portion of swelling smaller than that of the first portion.

5. The soft gripper according to claim 1, comprising:
   a first fixing element comprising a hook-and-loop fastener provided on an outer periphery at the leading end of the first actuator; and
   a second fixing element comprising a hook-and-loop fastener provided on an inner periphery at the leading end of the second actuator,
   wherein the first fixing element and the second fixing element are fixed to each other while overlapping each other when the object is surrounded by the first and second actuators.

6. The soft gripper according to claim 5, wherein
   a detaching fluid bag that receives the supply of the fluid from an outside to detach the first and second fixing elements from each other is disposed at positions corresponding to the first and second fixing elements.

7. The soft gripper according to claim 1, wherein
   a stretching fluid bag is provided along each surface side of the first and second actuators configured to come into contact with the object, so as to eliminate the bending of the first and second actuators and stretch the first and second actuators when the stretching fluid bag receives the supply of the fluid from an outside.

8. The soft gripper according to claim 1, wherein
   with respect to a width direction perpendicular to a longitudinal direction in which the first and second actuators extend, the side of the leading end of one of the first and second actuators is divided into two portions, and the side of the leading end of other of the first and second actuators is disposed between the two divided portions.

9. The soft gripper according to claim 1, wherein
with respect to a width direction perpendicular to a longitudinal direction in which the first and second actuators extend, the side of the leading end of one of the first and second actuators is divided into a plurality of portions, and the other side of the leading end of other of the first and second actuators is disposed between the plurality of divided portions.

10. The soft gripper according to claim 9,
wherein the object has an elongated shape in one direction,
the soft gripper further comprising:
a pressurization unit that sequentially pressurizes the first and second actuators from one side to the other side in an elongated direction of the object, wherein
the pressurization unit includes one flow path that receives the supply of the fluid from an outside to its one end, and at least one second throttle interposed between a portion connected to the first actuator in the flow path and a portion connected to the second actuator in the flow path.

11. The soft gripper according to claim 1, wherein in a state before the soft gripper is wound around the object, the first or second actuator has a shape bent or folded on an opposite side to a direction in which the object is surrounded.

12. The soft gripper according to claim 11, wherein the first or second actuator sequentially surrounds the object while releasing the bending or the folding.

13. A blood pressure measuring cuff comprising the soft gripper according to claim 1.

* * * * *